US009061045B2

(12) United States Patent
Choquet-Kastylevsky et al.

(10) Patent No.: US 9,061,045 B2
(45) Date of Patent: Jun. 23, 2015

(54) METHOD FOR PRONGF ASSAY FOR IN VITRO DIAGNOSIS OF CANCER IN PARTICULAR BREAST, THYROID OR LUNG CANCER AND THERAPEUTIC USE OF PRONGF

(75) Inventors: Geneviève Choquet-Kastylevsky, Francheville (FR); Yohann Demont, Lille (FR); Hubert Hondermarck, Villeneuve d'Ascq (FR)

(73) Assignees: BIOMERIEUX, Marcy l'Etoile (FR); UNIVERSITE DES SCIENCES ET TECHNOLOGIES DE LILLE, Villeneuve-d'Ascq (FR)

( * ) Notice: Subject to any disclaimer, the term of this patent is extended or adjusted under 35 U.S.C. 154(b) by 162 days.

(21) Appl. No.: 13/533,908

(22) Filed: Jun. 26, 2012

(65) Prior Publication Data
US 2013/0171173 A1 Jul. 4, 2013

Related U.S. Application Data

(60) Continuation of application No. 13/137,101, filed on Jul. 20, 2011, now abandoned, which is a division of application No. 12/087,606, filed as application No. PCT/FR2007/050708 on Jan. 30, 2007, now Pat. No. 8,008,009.

(30) Foreign Application Priority Data

Jan. 31, 2006 (FR) .................................. 06 00851

(51) Int. Cl.
*C07H 21/02* (2006.01)
*C07H 21/04* (2006.01)
*A61K 48/00* (2006.01)
*A61K 31/713* (2006.01)
*G01N 33/574* (2006.01)
*A61K 38/17* (2006.01)
*A61K 39/395* (2006.01)

(52) U.S. Cl.
CPC ........ *A61K 31/713* (2013.01); *G01N 33/57415* (2013.01); *G01N 2333/48* (2013.01); *A61K 38/177* (2013.01); *A61K 39/39558* (2013.01)

(58) Field of Classification Search
USPC ....................................... 514/2, 44; 536/24.5
See application file for complete search history.

(56) References Cited

U.S. PATENT DOCUMENTS

2001/0046959 A1 11/2001 Buchkovich et al.
2006/0051818 A1 3/2006 Adriaenssens et al.

FOREIGN PATENT DOCUMENTS

| WO | WO 03/076942 A2 | 9/2003 |
| WO | WO 2004/040312 A2 | 5/2004 |

(Continued)

OTHER PUBLICATIONS

Ebendal et al., Characterization of antibodies to synthetic nerve growth factor (NGF) and ProNGF peptides, J. Neurosci. Res., 22, 223-240, 1989.*

(Continued)

*Primary Examiner* — Terra C Gibbs
(74) *Attorney, Agent, or Firm* — Oliff PLC

(57) ABSTRACT

A ProNGF inhibitor for preparing a drug, said drug being in particular useful for blocking remote dissemination and cell invasion in patients suffering from cancer, in particular breast, thyroid or lung cancer.

16 Claims, 6 Drawing Sheets

(56) References Cited

FOREIGN PATENT DOCUMENTS

Figure 1:
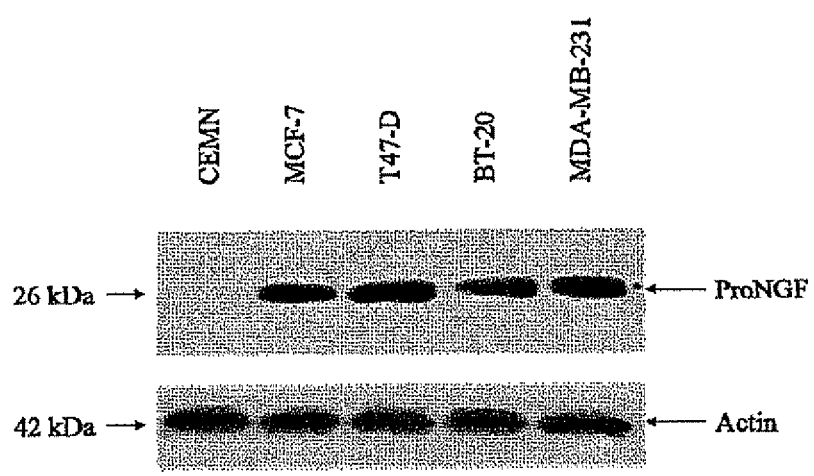

| WO | WO 2004/056385 A2 | 7/2004 |
|---|---|---|
| WO | WO 2005/076695 A2 | 8/2005 |

OTHER PUBLICATIONS

Lee et al., Regulation of Cell Survival by Secreted Proneurotrophins, Science, 294:1945-1948, 2001.*

Buttigieg et al. Neurotrophic activity of ProNGF in vivo, Exp. Neurol., 204, 832-835, 2007.*

Zips et al., New Anticancer Agents: In Vitro and In Vivo Evaluation, In vivo, 19, 1-8, 2005.*

Bierl et al., "'Mature' nerve growth factor is a minor species in most peripheral tissues," *Neuroscience Letters*, vol. 380, pp. 133-137, Jan. 2005.

Hasan et al. "Sympathetic Neurons Synthesize and Secrete Pro-Nerve Growth Factor Protein," *Journal of Neurobiology*, vol. 57, pp. 38-53, Apr. 2003.

Mazella et al., "The 100-kDa Neurotensin Receptor Is gp95/Sortilin, a Non-G-Protein-coupled Receptor," *The Journal of Biological Chemistry*, vol. 273, No. 41, pp. 26273-26276, Oct. 9, 1998.

Nykjaer et al., "Sortilin is essential for proNGF-induced neuronal cell death," *Nature*, vol. 427, pp. 843-848, Feb. 26, 2004.

Pedraza et al., "Pro-NGF Isolated from the Human Brain Affected by Alzheimer's Disease Induces Neuronal Apoptosis Mediated by p75NTR," *American Journal of Pathology*, vol. 166, No. 2, pp. 533-543, Feb. 2, 2005.

Descamps et al., "Nerve Growth Factor Is Mitogenic for Cancerous but Not Normal Human Breast Epithelial Cells," *The Journal of Biological Chemistry*, vol. 273, No. 27, pp. 16659-16662, Jul. 3, 1998.

Tagliabue et al., "Nerve Growth Factor Cooperates with p185$^{HER2}$ in Activating Growth of Human Breast Carcinoma Cells," *The Journal of Biological Chemistry*, vol. 275, No. 8, pp. 5388-5394, Feb. 25, 2000.

Dolle et al., "Nerve growth factor overexpression and autocrine loop in breast cancer cells," *Oncogene*, vol. 22, pp. 5592-5601, Aug. 28, 2003.

Fahnestock et al., "The Precursor Pro-Nerve Growth Factor Is the Predominant Form of Nerve Growth Factor in Brain and Is Increased in Alzheimer's Disease," *Molecular and Cellular Neuroscience*, vol. 18, No. 2, pp. 210-219, Aug. 2001.

Ebendal et al., "Characterization of Antibodies to Synthetic Nerve Growth Factor (NGF) and ProNGF Peptides," *Journal of Neuroscience Research*, vol. 22, pp. 223-240, 1989.

Lee et al., "Regulation of Cell Survival by Secreted Proneurotrophins," *Science*, vol. 294, pp. 1945-1948, 2001.

Buttigieg et al., "Neurotrophic Activity of proNGF in vivo," *Experimental Neurology*, vol. 204, pp. 832-835, 2007.

Zips et al., "New Anticancer Agents: In Vitro and In Vivo Evaluation," *In Vivo*, vol. 19, pp. 1-8, 2005.

\* cited by examiner

SEQUENCE LISTING

```
<160> NUMBER OF SEQ ID NOS: 6

<210> SEQ ID NO 1
<211> LENGTH: 21
<212> TYPE: RNA
<213> ORGANISM: Artificial
<220> FEATURE:
<223> OTHER INFORMATION: siGFP : in the sequence n represents t
      (thymine)
<220> FEATURE:
<221> NAME/KEY: misc_feature
<222> LOCATION: (20)..(21)
<223> OTHER INFORMATION: n is a, c, g, or u

<400> SEQUENCE: 1
gcugacccug aaguucaucn n                                              21

<210> SEQ ID NO 2
<211> LENGTH: 21
<212> TYPE: RNA
<213> ORGANISM: Artificial
<220> FEATURE:
<223> OTHER INFORMATION: siGFP : in the sequence n represents t
      (thymine)
<220> FEATURE:
<221> NAME/KEY: misc_feature
<222> LOCATION: (20)..(21)
<223> OTHER INFORMATION: n is a, c, g, or u

<400> SEQUENCE: 2
gaugaacuuc agggucagcn n                                              21

<210> SEQ ID NO 3
<211> LENGTH: 21
<212> TYPE: RNA
<213> ORGANISM: Artificial
```

```
<220> FEATURE:
<223> OTHER INFORMATION: siSORT : in the sequence n represents t
      (thymine)
<220> FEATURE:
<221> NAME/KEY: misc_feature
<222> LOCATION: (20)..(21)
<223> OTHER INFORMATION: n is a, c, g, or u

<400> SEQUENCE: 3
gguguguuua acagcagagn n                                                  21

<210> SEQ ID NO 4
<211> LENGTH: 21
<212> TYPE: RNA
<213> ORGANISM: Artificial
<220> FEATURE:
<223> OTHER INFORMATION: siSORT : in the sequence n represents t
      (thymine)
<220> FEATURE:
<221> NAME/KEY: misc_feature
<222> LOCATION: (20)..(21)
<223> OTHER INFORMATION: n is a, c, g, or u

<400> SEQUENCE: 4
cucugcuguu aacaccaccn n                                                  21

<210> SEQ ID NO 5
<211> LENGTH: 21
<212> TYPE: RNA
<213> ORGANISM: Artificial
<220> FEATURE:
<223> OTHER INFORMATION: siProNGF : in the sequence n represents t
      (thymine)
<220> FEATURE:
<221> NAME/KEY: misc_feature
<222> LOCATION: (20)..(21)
<223> OTHER INFORMATION: n is a, c, g, or u

<400> SEQUENCE: 5
caguguauuc aaacaguaun n                                                  21

<210> SEQ ID NO 6
<211> LENGTH: 21
<212> TYPE: RNA
<213> ORGANISM: Artificial
<220> FEATURE:
<223> OTHER INFORMATION: siProNGF : in the sequence n represents t
      -thymine)
<220> FEATURE:
<221> NAME/KEY: misc_feature
<222> LOCATION: (20)..(21)
<223> OTHER INFORMATION: n is a, c, g, or u

<400> SEQUENCE: 6
guacuguuug aauacacugn n                                                  21
```

METHOD FOR PRONGF ASSAY FOR IN VITRO DIAGNOSIS OF CANCER IN PARTICULAR BREAST, THYROID OR LUNG CANCER AND THERAPEUTIC USE OF PRONGF

This is a Continuation of application Ser. No. 13/137,101 filed Jul. 20, 2011, which is a Division of application Ser. No. 12/087,606 filed Jul. 10, 2008, which in turn is a National Phase of PCT/FR2007/050708, filed Jan. 30, 2007. The disclosures of the prior applications are hereby incorporated by reference herein in their entirety.

The present invention relates to the cancerology field. More particularly, the present invention relates to a method for diagnosing cancer, and more particularly breast, thyroid, lung or prostate cancer, in a human patient by in vitro determination of the presence of the nerve growth factor precursor (ProNGF) in a biological sample derived from this patient, or in the patient's tumor in vivo, it being possible for said method to be used for early diagnosis, screening, therapeutic follow-up and prognosis, and also for diagnosing relapses in cancer. Furthermore, due to the capacity of cancer cells, and more particularly breast, thyroid, lung or prostate cancer cells, for producing ProNGF, the present invention also relates to therapy.

In women, breast cancer is the most common cause of mortality due to cancer in industrialized countries. It is estimated that the minimum size of a tumor that can be detected by mammography is a few millimeters (mm). Breast cancers develop slowly. Nevertheless, at the time this small tumor is diagnosed, it has already been evolving for on average 8 years. The etiology of breast cancer is not well defined. Familial predispositions have been demonstrated. Age is the most important risk factor. Thus, the risk increases by 0.5% per year of age in western countries. Other risk factors are known, such as the number of pregnancies and the age at the first pregnancy, breast feeding, the age at puberty and at menopause, oestrogenic treatments after the occurrence of the menopause, stress and nutrition.

The test that is available and used in mass screening for breast cancer is an imaging technique: mammography. By virtue of this technique, mortality due to breast cancers has greatly decreased (30% reduction in mortality), which underlines the importance of tumor screening in terms of public health. Nevertheless, the screening techniques suffer from a certain number of handicaps. Mammography requires high-performance equipment and qualified personnel, which is expensive in the context of mass screening.

Thyroid cancer is a rare cancer. It represents approximately 1% of cancers occurring in the general population in France. Its annual incidence is low, i.e. approximately 2.5 per 100 000 individuals (Cancers: évaluation, traitement et surveillance [Cancers: assessment, treatment and monitoring]. J M Andrieu & P Colonna Ed. ESTEM, Paris 1997). The number of new cases of thyroid cancer in the United States in 2006 is estimated at 30 000, and the deaths at 1500 (American Cancer Society.: Cancer Facts and Figures 2006. Atlanta, Ga.: American Cancer Society, 2006).

Thyroid cancer usually develops in the form of a nodule located within the thyroid gland, whether it is of normal size or enlarged (goitre). It is a rare cancer, more common in young individuals, for which the prognosis is good when the cancer is in its papillary form since recovery occurs in 90% of cases.

The prevalence of the thyroid nodule is variable according to the screening means. It is more common in women, elderly individuals, and individuals who live in an area where there is an iodine deficiency or who have undergone irradiation of the cervical region during infancy, but these nodules are benign in more than 90% of cases. Young individuals are more exposed to development of the cancer due to a greater sensitivity of the thyroid to irradiation.

According to the international histological classification, a distinction can be made between four main histological types of thyroid carcinoma:
papillary epitheliomas,
follicular epitheliomas,
medullary epitheliomas,
anaplastic (or undifferentiated) epitheliomas.

These tumors may be solitary or multifocal.

The papillary cancers are more common. They predominate in young individuals and represent approximately 80% of thyroid cancers.

The follicular cancers represent approximately 10% of thyroid cancers and are especially common around the age of about forty.

The papillary and follicular cancers represent the group of radiosensitive differentiated thyroid cancers. They secrete thyroglobulin.

The medullary cancers represent 5% of thyroid cancers and correspond to a tumor of the C or parafollicular cells derived from the neural crest. The C cells secrete calcitonin.

The anaplastic or undifferentiated cancers are rare (less than 5% of cases) and extremely serious.

In the presence of a malignant thyroid nodule, the basic treatment is surgery.

If residual functional tissue remains, a dose of iodine 131 is administered in an isolated chamber, 4 to 6 weeks after a total thyroidectomy, in order to entirely sterilize it.

Approximately forty percent of thyroid cancer metastases fix iodine and can therefore be treated by this method.

After total thyroidectomy and sterilization of the thyroid with iodine 131, thyroxine, a hormone which inhibits TSH secretion, is administered. This hormone therapy also makes it possible to ensure a satisfactory thyroid balance in functional terms.

The discovery of new diagnostic and prognostic markers and of a targeted therapeutic agent could make it possible to complete the therapeutic and diagnostic arsenal for this cancer.

Lung cancer, which is responsible for more than 25 000 new cases each year in France, can be considered to be a major public health problem. It is the most common cancer in men and in fact represents the most common cause of mortality due to cancer in men and the third most common cause in women. The number of new cases of lung cancer (non small cell and small cell combined) in the United States in 2006 is estimated at 174 470, and deaths at 162 460 (American Cancer Society.: Cancer Facts and Figures 2006. Atlanta, Ga.: American Cancer Society, 2006).

Within the primary cancers, examination of the cancer cells (anatomopathological examination) makes it possible to draw a distinction between:
Epidermoid cancers (35-40%);
Adenocarcinomas (25-35%);
Large cell carcinomas (10-15%);
Small cell carcinomas (20-25%).

These four categories represent close to 95% of lung cancers. The first three are grouped together as "non small cell lung cancer" (NSCLC).

Small cell cancer progresses much more rapidly and is more likely to spread to other organs.

Carcinoid tumors and muco epidermoid tumors are more rare, and represent the remaining 1 to 2%.

These classifications can be summarized as "small cell lung cancer" (13%) or "non small cell lung cancer" (87%) with different therapeutic implications.

Efforts at early detection have not been shown to be effective with the current tools (lung X-ray, analysis of sputum and fibroscopy do not improve survival). It is possible that the spiral scan or molecular analyses of sputum may allow earlier detection, with cancers that can be more readily resected. However, no screening tool has yet been discovered, due in particular to the risks attached to lung biopsies and to surgery, especially in patients who are smokers.

Without treatment, small cell lung cancer is the most aggressive of the lung tumors, with a median survival of only 2 to 4 months. Compared with other types of lung cancer, small cell lung cancer has a tendency toward dissemination before diagnosis, but it is more sensitive to chemotherapy and to radiotherapy.

Non small cell lung cancer (NSCLC) covers various histologies. The most common histologies are epidermoid or squamous carcinoma, adenocarcinoma and large cell carcinoma. These histologies are often classified together because the approaches to diagnosis, grading, establishment of prognosis, and treatment are similar. Patients presenting a resectable cancer can be cured by surgery or surgery with adjuvant chemotherapy. Local control of the disease can be carried out with radiotherapy in a large number of patients with a nonresectable cancer. Patients presenting a locally advanced and nonresectable disease may have a long-term survival with radiotherapy combined with chemotherapy. Patients presenting advanced metastatic disease may experience an improvement of symptoms and of survival with chemotherapy.

At diagnosis, patients with NSCLC can be divided up into three groups of similar treatment. The first group of patients comprises surgically resectable tumors (generally stage I, stage II and certain stage III patients). This group has the best prognosis. Patients presenting a resectable cancer with medical contraindications for surgery are candidates for curative radiotherapy.

The second group includes patients with a locally (T3-T4) and/or regionally (N2-N3) advanced lung cancer.

The third group includes patients with remote metastases (M1) which were found at the time of diagnosis. This group can be treated with palliative radiotherapy or chemotherapy.

Multiple studies have tried to identify determining prognostic factors (Albain K S, Crowley J J, LeBlanc M, et al.: Survival determinants in extensive-stage non-small-cell lung cancer: the Southwest Oncology Group experience. J Clin Oncol 9 (9): 1618-26, 1991; Macchiarini P, Fontanini G, Hardin M J, et al.: Blood vessel invasion by tumor cells predicts recurrence in completely resected T1 N0 M0 non-small-cell lung cancer. J Thorac Cardiovasc Surg 106 (1): 80-9, 1993; Ichinose Y, Yano T, Asoh H, et al.: Prognostic factors obtained by a pathologic examination in completely resected non-small-cell lung cancer. An analysis in each pathologic stage. J Thorac Cardiovasc Surg 110 (3): 601-5, 1995; Martini N, Bains M S, Burt M E, et al.: Incidence of local recurrence and second primary tumors in resected stage I lung cancer. J Thorac Cardiovasc Surg 109 (1): 120-9, 1995; Fontanini G, Bigini D, Vignati S, et al.: Microvessel count predicts metastatic disease and survival in non-small cell lung cancer. J Pathol 177 (1): 57-63, 1995). The factors which correlate with an unfavorable prognosis include the following:

Presence of pulmonary symptoms.
Large size of the tumor (>3 centimeters).
Non epidermoid histology.
Node metastases in the lymph nodes, established by TNM.
Vascular invasion.

Similarly, contradictory results concerning the prognostic importance of the abnormal expression of a certain number of proteins in lung cancers have been reported. For patients with an inoperable cancer, the prognosis is compromised by a poor general condition and a weight loss of >10%.

Since the treatment is not satisfactory for almost all patients with NSCLC, it is necessary to discovery new therapeutic targets, and new tools for early diagnosis.

Prostate cancer is the most common cancer in men over the age of 50 and represents the second most common cause of death due to cancer in men in the developed world, after lung cancer.

Its incidence increases with age. In France, the overall incidence in 1990 was 71.4 per 100 000 (2.6 in the 35-49 year old age range; 133.8 in the 50-69 year old age range; 726.9 in the 70 year old age range). The average age for prostate cancer is around 70 years old, but some men are affected at an earlier age.

The 23% increase in mortality linked to prostate cancer over the past twenty years reflects the increase in life expectancy and the more frequent recognition of prostate cancer as principle cause of death. In France, the overall mortality due to cancer was 33.4 for 100 000 in 1990, i.e. more than 9000 deaths per year. Prostate cancer represents 3.4% of all deaths and 10.7% of deaths due to cancer.

Prostate cancer often develops very slowly, and remains localized at the beginning. When the cancer progresses, it can spread out of the prostate by direct invasion of the tissues and organs located close to the prostate, and it can spread into other organs remote from the prostate.

Prostate Specific Antigen (PSA) is a tumor marker used for detecting prostate cancer. The level of PSA in the blood is expressed in nanograms per milliliters (ng/ml) and is considered to be normal if the level is less than 4 ng/ml. The higher the PSA level in the case of prostate cancer, the greater the risk of remote spreading of the cancer, which usually means a decrease in the chances of recovery or long-term survival. Nevertheless, PSA is not the ideal marker: this is because certain cancers detected by an increased PSA level could have had a very slow progression, without the need for treatment. It is therefore essential to discover new diagnostic tools (for diagnosis at the tissue level or at the level of biological fluids), in order to precisely detect cancers with an aggressive potential, to redistinguish from cancers with a very slow progression.

In order to specify the diagnosis, endorectal echography of the prostate is used, which can very precisely guide a needle in order to take samples at a given site in the prostate. Only biopsy can confirm cancer, since the cancer cells are visible under the microscope. Biopsies are therefore of essential importance for determining the prognosis of the disease.

The reference treatment is radical prostatectomy. This operation removes the entire prostate and the seminal vesicles. It is only carried out if the cancer does not exceed the limits of the prostate. Approximately 10% of patients will develop a local recurrence within 5 years following a radical prostatectomy for localized prostate cancer.

Radiotherapy is used to treat cancers which are localized in the prostate, or which have reached the neighboring tissues. It can be used to reduce the tumor volume or to prevent local complications.

The objective of hormone treatment is to oppose the action of the male hormones (androgens) which stimulate, the prostate. Thus, decreasing the level of testosterone, the main male hormone, blocks the proliferation of the cancer cells and reduces the volume of the prostate. Hormone treatment only has a transient effect; it blocks the proliferation of the cancer without curing it.

Chemotherapy is used in prostate cancer when the latter has progressed with spreading outside the prostate and no longer responds to hormone treatment. Chemotherapy reduces the tumor growth and can reduce the pain associated with the cancer.

The treatments mentioned above may have a certain number of side effects, including urinary incontinence, impotence, intestinal problems (diarrhea, colitis), and urinary problems occurring essentially during the treatment (frequency of urination, weakened urine stream, urgent need to urinate, burning sensation when urinating, presence of blood in the urine). Long-term hormone treatment can lead to osteoporosis with bone becoming brittle.

New targeted therapeutics could make it possible to prevent a certain number of these side effects, and to improve the effectiveness of the treatment for prostate cancer. New diagnostic and prognostic tools could make it possible to differentiate between slowly progressing cancers and aggressive cancers with metastatic potential.

In clinical practice, the characterization of a tumor in terms of malignancy is carried out, after the tumor has been discovered, by histological methods in specialized laboratories. A set of parameters such as the size of the tumor, its histopathological grade, associated inflammation and lymph node invasion are used to decide on the therapy and to estimate the prognosis of the disease.

Markers which make it possible to distinguish between tumor cells and normal cells have been sought and studied for years, for many cancers, including breast, thyroid, lung and prostate cancer. They would make it possible to diagnose the disease early, to establish the prognosis for said disease and the sensitivity to treatment, and to monitor the progression of said disease. Up until now, the candidate markers which have been identified and studied have been oncogenes, tissue markers and markers associated with angiogenesis or with the metastatic capacities of the tumor. Currently, the breast cancer markers identified are mainly used for therapeutic follow-up. There is no validated biological test for the early diagnosis or for the screening of breast cancer, nor is there one for many other cancers (for the mass screening of colorectal cancer, there is the detection of hemoglobin in the stools). PSA can be used to aid the diagnosis and to indicate the need for a prostate biopsy in the case of prostate cancer. Immunoassay for calcitonin in the plasma is an excellent marker for medullary thyroid cancers. In certain countries, it may be used for screening for prostate cancer, but it has not been validated on a population base for this indication. Only the detection of oestrogen receptors on breast tumor tissue makes it possible to determine whether the breast tumors will or will not be hormone-sensitive. Detection of the HER-2/neu receptor in breast cancers makes it possible to determine whether the tumor is sensitive to Herceptin.

A limited number of antigenic markers, in particular CA 15-3 (Basuyau, J. P., M. P. Blanc-Vincent, J. M, Bidart, A. Daver, L. Deneux, N. Eche, G. Gory-Delabaere, M. F. Pichon, and J. M. Riedinger. 2000. [Standards, Options and Recommendations (SOR) for tumor markers in breast cancer. SOR Working Group]. Bull Cancer. 87:723-37) has been identified in the case of cancerous breast cells. It is common practice for this marker to be used for patient follow-up, in particular for the detection of recurrence, but, because of its low sensitivity, it is not proposed in either a screening test or diagnostic test.

For several years, studies relating to the antigens associated with breast cancer have been developed, not in order to look for markers, but in order to look for targets for immunotherapy. These studies range from the demonstration of a humoral immunity against T/Tn antigens (Springer, G. F. 1997. Immunoreactive T and Tn epitopes in cancer diagnosis, prognosis, and immunotherapy. J Mol. Med. 75:594-602), to the more recent discovery of antibodies and of T-cell responses directed against p53 (Gnjatic, S., Z. Cai, M. Viguier, S. Chouaib, J. G. Guillet, and J. Choppin. 1998. Accumulation of the p53 protein allows recognition by human CTL of a wild-type p53 epitope presented by breast carcinomas and melanomas. J. Immunol. 160:328-33) and HER-2/neu (Disis, M. L., and M. A. Cheever. 1997. HER-2/neu protein: a target for antigen-specific immunotherapy of human cancer. Adv Cancer Res. 71:343-71).

More recently, a series of new potential antigens has been revealed by the SEREX (serological expression cloning) approach, based on the construction of cDNA libraries of tumor cells and screening with the autologous serum. Serological breast cancer library screening has thus made it possible to reveal the ING1 antigen (Jager, D., E. Stockert, M. J. Scanlan, A. O. Gure, E. Jager, A. Knuth, L. J. Old, and Y. T. Chen. 1999. Cancer-testis antigens and ING1 tumor suppressor gene product are breast cancer antigens: characterization of tissue-specific ING1 transcripts and a homologue gene. Cancer Res. 59:6197-204.), and then a new differentiation antigen, NY-BR-1, expressed, according to the authors, in 80% of breast cancers and inducing the production of IgG antibodies in the patients (Jager, D., E. Stockert, A. O. Gure, M. 3. Scanlan, J. Karbach, E. Jager, A. Knuth, L. J. Old, and Y. T. Chen. 2001. Identification of a tissue-specific putative transcription factor in breast tissue by serological screening of a breast cancer library. Cancer Res. 61:2055-61). This type of approach, which has mainly been used to search for targets that can potentially be used for developing vaccines, does not, a priori, exclude the antigens present in normal tissue (this is the case of NY-BR-1), nor those recognized by a limited number of sera from patients (2/14 for ING1); they cannot therefore be exploited for a screening or early diagnosis strategy. By means of the same approach, other antigens inducing a humoral immune response in patients have been revealed, such as NY-BR-62, NY-BR-85 and the D52 protein. These antigens are thought to be overexpressed respectively in 60%, 90% and 60% of breast cancers (Scanlan, M. J., and D. Jager. 2001. Challenges to the development of antigen-specific breast cancer vaccines. Breast Cancer Res. 3:95-8.).

The molecular phenomena which result in the development of cancers, and more particularly of a breast cancer, involve modifications of the structure and of the expression of oncogenes (such as ras) and mutations of tumor-suppressor genes such as p53. The growth of tumor cells in the majority of breast cancers is dependent on oestrogenic hormones (oestradiol and progesterone) and on growth factors which control proliferation, migration and apoptosis. The growth of prostate cancers is androgen-dependent. The growth of certain thyroid cancers is thyroid stimulating hormone (TSH)-dependent. These growth factors either stimulate or inhibit the proliferation, migration and differentiation of the tumor cells in such a way as to act in concert so as to promote the growth of the cancer and the metastases. For example, insulin-type growth factors, transforming growth factor α (TGF-α) and fibroblast growth factors (FGFs) can all stimulate the proliferation of breast cancer cells, while mammary-derived growth factor inhibiter (MDGI) and transforming growth factor β (TGF-β) inhibit their growth.

In patent application WO2004/040312, the Applicants have described the use of NGF as a tumor marker and as a therapeutic target. Thus, NGF is produced by breast cancer cells, whereas corresponding normal mammary epithelial cells do not produce it. Furthermore, NGF stimulates the survival and proliferation of cancerous mammary epithelial cells, whereas it has no effect on normal mammary epithelial cells.

The NGF gene encodes a protein precursor called ProNGF (26 kDa) which, by enzymatic cleavage, generates NGF (13.6 kDa) (Seidah et al., 1996, Biochem J., 314: 951-960). The main source of NGF in mammals is the submaxillary gland, which contains only NGF and very little ProNGF. For a long time, the only role given to ProNGF was a role as a metabolic precursor with a very transient life time.

More recently, it has been shown, in various tissues, that ProNGF is found in an amount of greater than that of NGF (Bierl et al., 2005, Neurosci Lett, 380: 133-137). Hasan et al. have described that ProNGF can be secreted, which means that it can potentially act in an autocrine, paracrine or even endocrine manner (2003, J Neurobiol, 57: 38-53). Finally, it has recently been demonstrated that ProNGF has, at the surface of neuronal cells, a high-affinity binding site through which it has specific effects, different than those of NGF. Thus, ProNGF is capable of binding to sortilin, a glycoprotein of 100 kDa (Mazella et al., 1998, J Biol Chem, 273: 26273-26276), and of inducing neuronal cell apoptosis in vitro (Nykjaer et al., 2004, Nature, 427: 843-848). Patent applications WO 2004/056385 and WO 2005/076695 show that the interaction between a neurotrophin (NGF or ProNGF) can be modified using specific compounds, such a modulation allowing the treatment of pain associated with certain diseases of the urogenital system or of patients whose nervous system has been damaged. An in viva pro-apoptotic activity has also been attributed to ProNGF (Pedraza et al., 2005, Am J Pathol, 166: 533-543). It is clear that there is a separation in terms of the expression and the biological effects of NGF and of ProNGF, which appear to be different.

More generally, propeptides have for a long time been considered to be only metabolic precursors; a certain number of recent examples, in particular in the neuropeptide field, indicate that, in certain situations, propeptides have their own biological activity, dissociated from that of the mature peptide that they are able to generate. This is clearly the case of ProNGF, which can be secreted by the cell, has its own receptors and is shown to have biological effects different than those of NGF on neurons. ProNGF thus constitutes a specific molecular and biological entity different than NGF. Admittedly, the sequence of NGF is contained in that of ProNGF, but their isoelectric points and molecular weights are different, as are their biological activities.

The Applicants have now demonstrated, surprisingly, that epithelial cancer cells, and in particular epithelial breast, thyroid, lung and prostate cancer cells, themselves produce and secrete ProNGF, in notable amounts, whereas normal epithelial cells of the same organs do not produce it, such that ProNGF can be used as a tumor marker or else as a therapeutic target. The Applicants have also established that ProNGF overexpressed in cancer cells has a prometastatic activity for these cells, whereas NGF, for its part, has an anti-apoptotic and mitogenic activity.

Thus, a first subject of the present invention is a method for in vitro diagnosis of cancer, and in particular breast, thyroid, lung or prostate cancer, by determining the presence of ProNGF in biological samples derived from patients suspected of suffering from cancer, and in particular breast, thyroid, lung or prostate cancer.

The method of the invention thus makes it possible to diagnose the cancer, and in particular breast, thyroid, lung or prostate cancer, by means of a simple test consisting in searching for the presence of ProNGF in a biological sample taken from a patient, or in the patient's tumor in vivo. The Applicants have shown, unexpectedly, that cancerous cells produce ProNGF, whereas the corresponding noncancerous cells are incapable of doing so, as will be demonstrated in more detail hereinafter. Thus, the determination of the presence of ProNGF in the sample makes it possible to conclude that the pathology being sought is present, the absence of ProNGF making it possible to conclude that the pathology is absent. The presence of ProNGF in the tumors may also be shown in vivo, in situ in the tumors.

In order to show the presence of ProNGF in a tumor in viva, any imaging method known to those skilled in the art can be used. For this, a specific ProNGF binding partner can be coupled to an imaging tracer. The specific ProNGF binding partners are any partner capable of binding to ProNGF. By way of example, mention may be made of antibodies, antibody fractions, receptors and any other molecule capable of binding to ProNGF.

The binding-partner antibodies are, for example, either polyclonal antibodies or monoclonal antibodies.

The expression "coupling of binding partners to an imaging tracer" is intended to mean the attachment of a tracer that can be detected by any imaging method known to those skilled in the art, and that can directly or indirectly generate a detectable signal. Thus, the tracer may be a radioactive tracer such as technetium-99. In this case, the organ affected by the primary cancer or the metastases will bind the ProNGF and its tracer. The radiation emitted by the organ can be filmed by a special camera, for example a gamma-camera. The apparatus collects the scintillations generated by the radioactive substance and thus makes it possible to visualize the organ.

In another method of the invention, the tracer comprises a positron-emitting radioactive substance (fluorine 18). The images will then be captured by a Positron Emission Tomography system.

In another preferred method of the invention, the ProNGF partner may be coupled to nanoparticles. By way of example, they may be supramagnetic nanoparticles; for example, anionic magnetic nanoparticles for use in direct cell labeling and in vivo detection by nuclear magnetic resonance imaging. They may also be gold nanoparticles. By virtue of the methods of the invention that make it possible to detect ProNGF in vivo, the areas of the body where there has been binding of the ProNGF binding partner, cancers producing ProNGF, in particular breast, prostate, thyroid and lung cancers, and also the locations of their remote metastases and the lymph node involvements may be visualized.

The determination of the presence of ProNGF in vitro can be carried out by direct detection of the ProNGF, by culturing cells sensitive to ProNGF, or by any other method for determining the presence of a protein in the sample, known to those skilled in the art.

The determination of the presence of ProNGF by direct detection of the ProNGF constitutes a specific embodiment of the invention.

The term "direct detection of the ProNGF" is intended to mean the demonstration of the ProNGF itself in the biological sample.

The direct detection of the ProNGF in the biological sample can be carried out by any means known to those skilled in the art, such as, for example, by immunoassay or by mass spectrometry, which constitutes a specific embodiment of the invention.

The immunoassay may be any assay widely known to those skilled in the art involving immunoreactions, namely reactions between the ProNGF and a specific ProNGF binding partner.

The specific ProNGF binding partners are any partner capable of binding to ProNGF. By way of example, mention may be made of antibodies, antibody fractions, receptors and any other molecular capable of binding to ProNGF.

The binding-partner antibodies are, for example, either polyclonal antibodies or monoclonal antibodies.

The polyclonal antibodies may be obtained by immunization of an animal with ProNGF, followed by recovery of the desired antibodies in purified form, by taking a sample of the serum of said animal and separating said antibodies from the other serum constituents, in particular by affinity chromatography on a column to which an antigen specifically recognized by the antibodies, in particular ProNGF, is attached. The monoclonal antibodies may be obtained by the hybridoma technique, the general principle of which is summarized below.

Initially, an animal, generally a mouse (or cells in culture in the case of in vitro immunizations), is immunized with ProNGF, and the B lymphocytes of said animal are then capable of producing antibodies against said antigen. These antibody-producing lymphocytes are subsequently fused with "immortal" myeloma cells (murine in the example) so as to produce hybridomas. From the heterogeneous mixture of cells thus obtained, a selection of the cells capable of producing a particular antibody and of multiplying indefinitely is then made. Each hybridoma is multiplied in the form of a clone, each one resulting in the production of a monoclonal antibody whose properties of recognition with respect to ProNGF may be tested, for example, by ELISA, by one- or two-dimensional immunoblotting, by immunofluorescence, or using a biosensor. The monoclonal antibodies thus selected are subsequently purified, in particular according to the affinity chromatography technique described above.

The monoclonal antibodies may also be recombinant antibodies obtained by genetic engineering, by techniques well known to those skilled in the art.

Examples of anti-ProNGF antibodies are known and are available in particular in the Chemicon catalog.

The specific ProNGF binding partners may be labeled for visualization of the ProNGF/binding partner binding when the binding partner is used as a detection reagent, and therefore for the direct detection of ProNGF in the biological sample.

The term "labeling of the binding partners" is intended to mean the attachment of a label capable of directly or indirectly generating a detectable signal. A nonlimiting list of these labels consists of:

enzymes which produce a signal detectable, for example, by colorimetry, fluorescence or luminescence, such as horseradish peroxidase, alkaline phosphatase, α-galactosidase or glucose-6-phosphate dehydrogenase,
  chromophores such as fluorescent, luminescent or dye compounds,
  radioactive molecules such as $^{32}P$, $^{35}S$ or $^{125}I$, and
  fluorescent molecules such as Alexas or phycocyanins.

Indirect systems may also be used, for instance ligands capable of reacting with an antiligand. The ligand/antiligand pairs are well known to those skilled in the art, which is the case, for example, of the following pairs: biotin/streptavidin, hapten/antibody, antigen/antibody, peptide/antibody, sugar/lectin, polynucleotide/sequence complementary to the polynucleotide. In this case, it is the ligand which carries the binding partner. The antiligand may be directly detectable by virtue of the markers described in the previous paragraph or may itself be detectable by means of a ligand/antiligand.

These indirect detection systems may, under certain conditions, result in an amplification of the signal. This signal amplification technique is well known to those skilled in the art, and reference may be made to prior patent applications FR98/10084 or WO-A-95/08000 by one of the Applicants, or to the article J. Histochem. Cytochem. 45: 481-491, 1997.

Depending on the type of labeling used, those skilled in the art will add reagents for visualizing the labeling.

By way of example of immunoassays as defined above, mention may be made of "sandwich" methods such as ELISA, IRMA and RIA, "competition" methods and direct immunodetection methods such as immunohistochemistry, immunocytochemistry, Western blotting and Dot blots.

In the case of the "competition" methods, the ProNGF is labeled as described above for the binding partner.

Mass spectrometry may also be used for direct detection of ProNGF in the biological sample. The principle of spectrometry is widely known to those skilled in the art and is described, for example, in Patterson, S., 2000, Mass spectrometry and proteomics. Physiological Genomics 2, 59-65.

To do this, the biological sample, which may or may not be pretreated, is passed through a mass spectrometer and the spectrum obtained is compared with that of ProNGF. An example of a pretreatment of the sample consists in passing it over an immunocapture support comprising one of the ProNGF binding partners, for example an antibody directed against ProNGF. Another example of pretreatment of the sample may be prefractionation of the biological sample, in order to separate the proteins in the sample from one another. In techniques well known to those skilled in the art, the predominant proteins in the sample may, for example, first of all be depleted.

The biological sample used for the direct detection of ProNGF, which may contain ProNGF as such, may consist of biological fluid or a tissue originating from the biopsy of the tumor or of the metastases of the patient under consideration.

By way of biological fluid, mention may be made of whole blood and derivatives thereof, such as serum or plasma, bone marrow, milk, cerebrospinal fluid, urine and effusions. Blood or derivatives thereof is/are preferred.

For the detection of ProNGF, the biological fluid, which constitutes a specific embodiment of the invention, may require a specific treatment. This is because the biological fluid may contain ProNGF as such, or else it may contain circulating tumor cells which contain ProNGF, and/or circulating tumor cells which are capable of secreting ProNGF.

Thus, according to one embodiment of the invention, the biological fluid is pretreated in order to isolate the circulating tumor cells contained in said fluid.

The expression "to isolate the circulating tumor cells" is intended to mean to obtain a cell fraction enriched in circulating tumor cells.

The treatment of the fluid in order to isolate the circulating tumor cells may be carried out by cell sorting in a flow cytometer, by enrichment on Ficoll, by enrichment using magnetic beads coated with specific antibodies, or by any other method of specific enrichment known to those skilled in the art.

In the case of blood or bone marrow as biological fluid, the circulating tumor cells may be isolated by virtue of a technique of cell separation on Ficoll associated with depletion of the blood cells using anti-CD45 antibodies coupled to magnetic beads (Dynal Biotech ASA, Norway).

The direct detection of ProNGF can then be carried out directly on circulating to tumor cells isolated from the biological fluid, for example by immunocytochemical labeling of these cells with an anti-ProNGF antibody, after having deposited the circulating tumor cells onto a slide by cytospin. The direct detection of ProNGF can also be carried out directly in the circulating tumor cells by using the flow cytometry method as described in Métézeau P, Ronot X, Le Noan-Merdrignac G, Ratinaud M H, La cytometrie en flux pour l' etude de la cellule normale ou pathologique [Flow ctyometry for studying normal or pathological cells] (Tome I), published by Medsi-MacGrawhill.

Under these conditions, said circulating cells can be treated under conditions which allow the ProNGF to be blocked inside said cells. Such a treatment is described, for example, in Intracellular Flow Cytometry, Applied reagents and Techniques, pp 1-21, BD Pharmingen.

The detection of ProNGF is then carried out after having made the membrane of the cells permeable so as to enable the specific ProNGF binding partners to enter.

The direct detection of ProNGF using the circulating cells can also be carried out by means of the method described in patent application WO 03/076942 filed by one of the Applicants.

The direct detection of ProNGF in the tumor cells can also be carried out in the culture medium of said cells, after having cultured them under conditions such that they secrete ProNGF.

These culture conditions are conventional conditions, such as 37° C. in a humid atmosphere and at 5% $CO_2$.

When the biological sample to be tested is tissue originating from the biopsy of the tumor or of the metastases of the patient, which constitutes a specific embodiment of the invention, the direct detection of ProNGF is carried out directly on the sections obtained, without pretreatment of said tissue.

Another method of detecting the presence of ProNGF consists in culturing ProNGF-sensitive cells in the presence of the biological sample, which constitutes a specific embodiment of the invention.

In this case, the detection of the presence of ProNGF in a biological sample is demonstrated by the reaction of the ProNGF-sensitive cells.

The term "ProNGF-sensitive cells" is intended to mean any cell stimulated in the presence of ProNGF (growth, apotosis, etc.).

By way of ProNGF-sensitive cells, mention may be made of cells of neuronal origin, such as, for example, PC12 cells (Pedraza et al. Am. J. Pathol. 2005, 166, 533-543).

The biological sample that can be used for detecting the presence of ProNGF by culturing ProNGF-sensitive cells may be any sample as described above.

Thus, the biological sample may consist of biological fluid, where appropriate pretreated in order to isolate the circulating tumor cells, which themselves may subsequently be cultured under conditions such that they secrete ProNGF, as described above.

The method of the invention may be used both for early diagnosis and for screening, therapeutic follow-up, prognosis and diagnosing relapses in cancer, and in particular breast, thyroid, lung or prostate cancer, since only the cancerous cells produce ProNGF and this production depends on the grade of the cancer.

Thus, another subject of the invention consists of the use of the method of the invention in early diagnosis, screening, therapeutic follow-up, prognosis and diagnosing of relapses in cancer, and in particular breast, thyroid, lung or prostate cancer.

In addition to a tumor marker role, ProNGF may also have a role as a therapeutic target. In fact, due to the ability of cancerous cells, in particular breast, thyroid, lung or prostate cancer cells, to produce ProNGF, whereas normal cells do not produce it, the remote dissemination of breast, thyroid, lung or prostate cancer cells and the invasion of the cells can be blocked by a ProNGF inhibitor capable of blocking the activity of ProNGF.

Moreover, ProNGF, alone or in combination with other molecules, may be used as a therapeutic target for targeting therapeutic tools. The therapeutic tools may, in this case, be activatable nanoparticles, cytotoxic agents, or any other molecule which makes it possible to destroy cancerous cells.

The ProNGF inhibitors may therefore be used as drugs.

Thus, a subject of the present invention is also the use of a ProNGF inhibitor for preparing a drug, in particular in the treatment of cancer and more particularly breast, thyroid, lung or prostate cancer.

According to a specific embodiment of the invention, said drug can be used for blocking cell migration or the invasion of tumor cells in patients suffering from cancer, and more particularly breast, thyroid, lung or prostate cancer.

The term "cell migration" is intended to mean remote dissemination in patients suffering from cancer, and more particularly breast, thyroid, lung or prostate cancer (metastases), and the term "invasion" is intended to mean the local penetration of the cancerous cells.

The pharmaceutical compositions comprising, as active ingredient, at least one ProNGF inhibitor, optionally in combination with a pharmaceutically acceptable excipient, are also included in the invention.

The pharmaceutical compositions that can be used against cancer comprise, as active ingredient, at least one ProNGF inhibitor capable of blocking cell migration or invasion.

The term "ProNGF inhibitor" is intended to mean direct inhibitors of ProNGF, i.e. inhibitors that block the biological activity of the protein, such as the ProNGF binding partners, and also inhibitors of ProNGF receptors or any inhibitor of ProNGF signaling pathways, and also any molecule that can specifically bind to ProNGF, irrespective of whether or not there is blocking of the biological activity.

An example of a ProNGF receptor expressed in both tumoral and normal breast epithelial cells comprises Sortilin.

The specific ProNGF binding partners suitable as active ingredient are in particular as defined above in the immunoassays and may be any other partner known to those skilled in the art capable of blocking cell migration or invasion. According to a specific embodiment, the specific partner capable of blocking the migration or invasion of breast cancer cells is an anti-ProNGF antibody.

Another example of a direct inhibitor of ProNGF comprises the analogs, in soluble form, of ProNGF receptors, such as Sortilin analogs in soluble form, which also constitutes an embodiment of the invention.

The expression "inhibitor of ProNGF receptors expressed by both tumoral and normal breast epithelial cells" is intended to mean any molecules which block the activity of ProNGF, for example either via said receptor or by blocking its production. The blocking of ProNGF activity via said receptor may be carried out by preventing the binding of ProNGF to said receptor, for instance using an agent capable of binding to said receptor, which thus takes the place of the ProNGF. An example of such an inhibitor comprises a ProNGF-derived peptide which has conserved the properties of binding to said receptor or an antibody directed against the receptor. The activity of ProNGF may also be blocked by blocking the production of said receptor using inhibitors of the mRNA of said receptor or of the gene encoding said receptor. As an inhibitor of the receptor mRNA, use may be made of a synthetic fragment of this mRNA. In fact, interference RNA technology (Small Interference RNA or siRNA) is based on the use of a double-stranded RNA oligonucleotide corresponding to a short sequence of the cellular mRNA to be inhibited. This oligonucleotide in the form of a duplex (possibly introduced into a plasmid), after it has entered the cell, is dealt with by the Dicer/Risc enzyme system, which will bring about the degradation of the corresponding cellular mRNA (Dykxhoorn D et al., 2003, Nature Reviews, vol. 4, p457-467). By way of inhibitor of the gene encoding the receptor, mention may be made of an antisense oligonucleotide of said receptor. This oligonucleotide can be readily prepared by those skilled in the art (Lefrançois S et al. Biol. Proced. online. 2005, 7(1):17-25).

According to a specific embodiment of the invention, the ProNGF inhibitor is an siRNA of the ProNGF receptor.

The expression "ProNGF signaling pathway inhibitor" is intended to mean any molecule which blocks the biological activity of ProNGF, such as its activity on cell migration and invasion.

In order to target the therapeutic action of the various inhibitors, the latter may be placed under conditions such that they specifically penetrate into the cells of interest, for instance tumor cells, which constitutes another embodiment of the invention.

To this effect, they may, for example, be attached to a partner which allows such penetration, for instance a carrier molecule, a polymer such as the polymers used in gene therapy or else a viral vector such as adenoviruses and poxviruses, also used in gene therapy.

For example, in the case of breast cancer, the carrier molecule may be an anti-MUC1 antibody or an anti-epithelial cell antibody, or alternatively an anti-HER/2/neu antibody. In the case of thyroid cancer, the carrier molecule may be an anti-thyroglobulin antibody or an anti-epithelial cell antibody. In prostate cancer, the carrier molecule may be an anti-PSA antibody or an anti-epithelial cell antibody. In the case of lung cancer, the carrier molecule may be an anti-epithelial cell antibody.

The ProNGF signaling pathway inhibitors may also be attached to anticancer agents. The term "anticancer agent" is intended to mean a compound which will be toxic for the cancerous cell. For example, the ProNGF partners may be associated with therapeutic nanoparticles, which may allow the targeted destruction of the tumor when they are activated. In another method of the invention, the ProNGF partner may be coupled to a cytotoxic agent, or to a molecule for blocking a carcinogenic process.

Preferably, when the pharmaceutical composition comprises, as active ingredient, a ProNGF inhibitor such as a direct inhibitor or a ProNGF signaling pathway inhibitor, the latter are placed under conditions such that they specifically penetrate into the tumor cells of interest, the ProNGF mRNA inhibitors and the inhibitors of the gene encoding NGF having the ability to naturally penetrate into said cells.

The amount and the nature of the excipient may be readily determined by those skilled in the art. They are chosen according to the pharmaceutical form and the method of administration desired.

The pharmaceutical compositions of the invention are suitable for oral, sublingual, subcutaneous, intramuscular, intratumoral, intravenous, topical, local, intratracheal, intranasal, transdermal, rectal, intraocular or intra-auricular administration, it being possible for said active ingredient to be administered in unit administration form.

The unit administration forms may, for example, be tablets, gel capsules, granules, powders, injectable oral solutions or suspensions, patches, sublingual, buccal, intratracheal, intraocular, intranasal or intra-auricular administration forms, forms of administration by inhalation, topical, transdermal, subcutaneous, intramuscular, intratumoral or intravenous forms, rectal administration forms, or implants. For topical administration, creams, gels, ointments, lotions or eye lotions can be envisioned.

These galenical forms are prepared according to the usual methods in the fields under consideration.

Said units forms contain a dosage so as to allow daily administration of from 0.001 to 10 mg of active ingredient per kg of body weight, according to the galenical form.

There may be specific cases where higher or lower dosages are appropriate; such dosages do not depart from the scope of the invention. According to the usual practice, the dosage appropriate for each patient is determined by the physician according to the method of administration and the weight and response of the patient.

According to another embodiment, the present invention also relates to a method for treating breast cancer, which comprises the administration, to a patient, of an effective dose of a ProNGF binding partner or of a ProNGF inhibitor.

Figure 2:
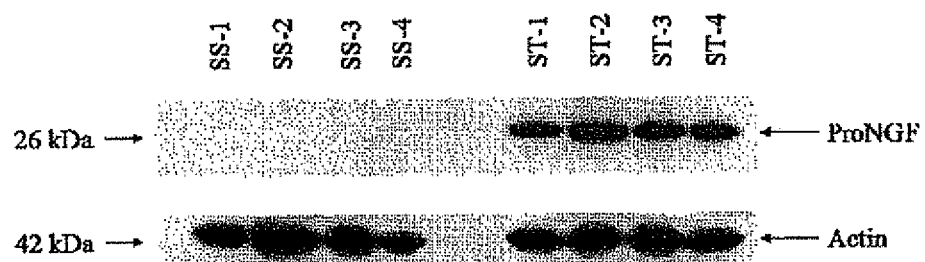
Figure 3:
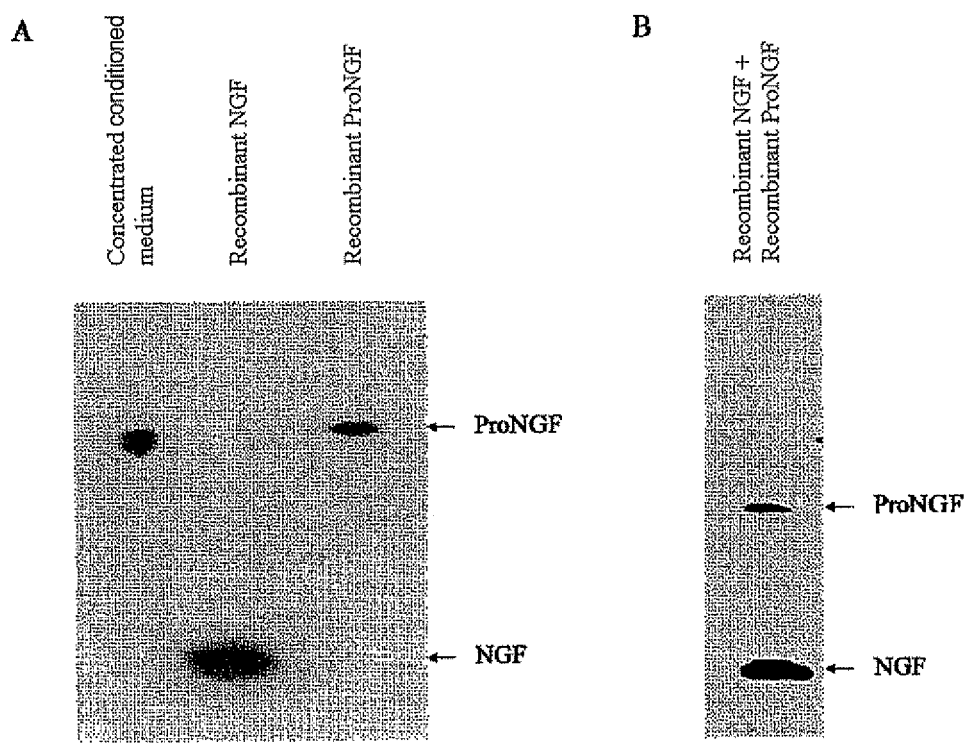
Figure 4:
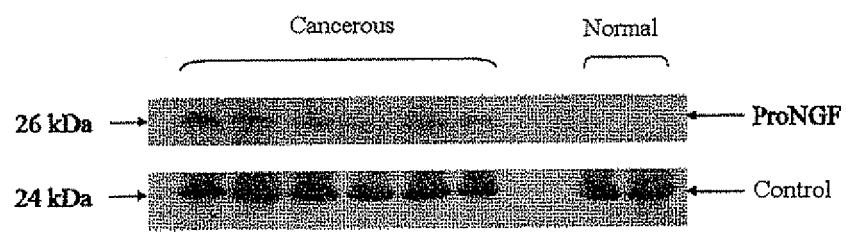
Figure 5:
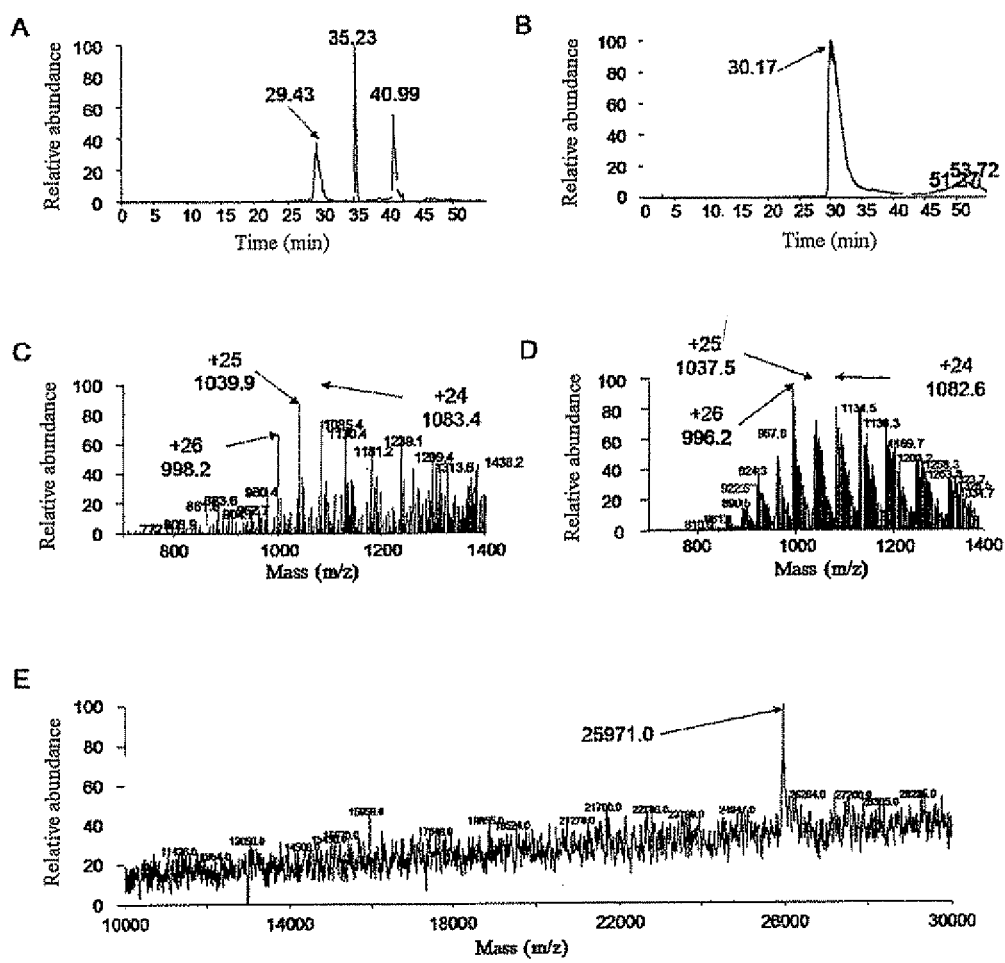
Figure 6:
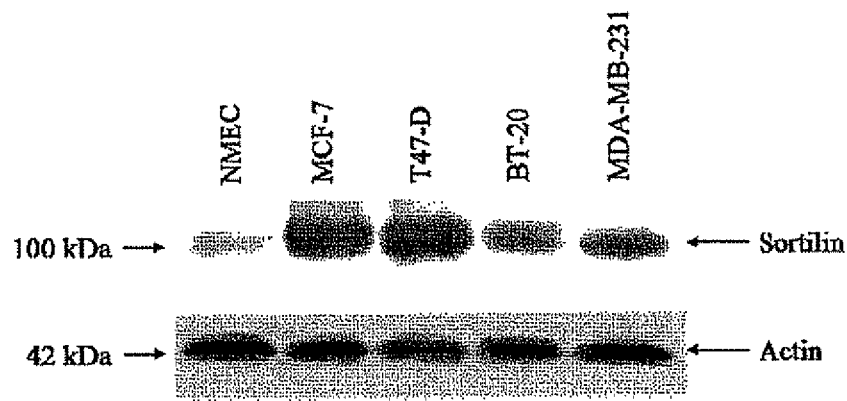
Figure 7:
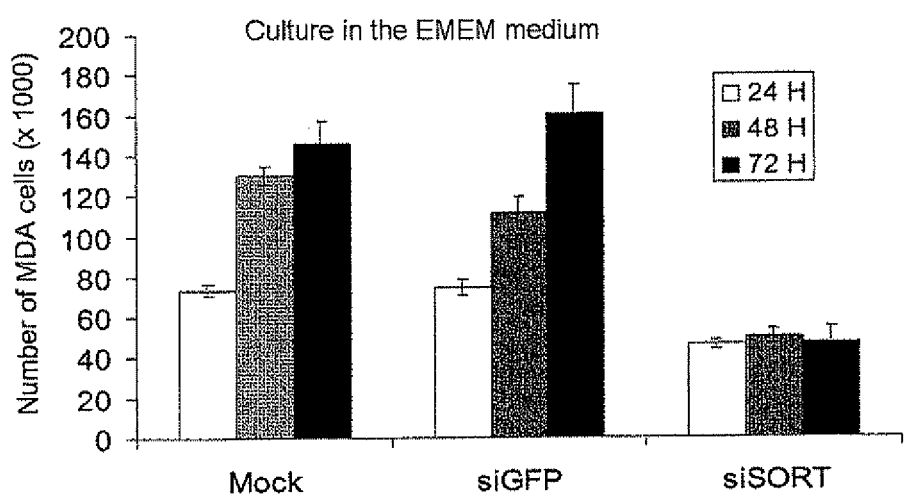

The invention will be understood more clearly from the following examples, given by way of nonlimiting illustration, and also from tables 1 and 2 and from attached FIGS. 1 to 10, on which:

FIG. 1 represents a photograph of a Western blot showing the production of ProNGF by cancerous mammary epithelial cells (MCF-7, T47-D, BT-20 and MDA-MB-231), but not by normal cells (NMEC cells), actin having been used as positive control, FIG. 2 represents a photograph of a Western blot showing the presence of ProNGF in the cancerous breast biopsies (ST-1 to -4) but not in the normal biopsies (SS-1 to -4), actin having been used as normalization control, FIG. 3 represents a photograph of a Western blot showing:

FIG. 3A: the secretion of ProNGF by MCF-7 cancerous cells (concentrated conditioned medium lane), the two lanes on the right being control lanes, FIG. 3B: that the concentrating/desalifying unit used for the experiment of FIG. 3A was capable of retaining NGF, FIG. 4 represents a photograph of a Western blot showing the presence of ProNGF in the sera of mice injected with cancerous cells and its absence in the sera of normal mice, FIG. 5 represents graphs of detection by mass spectrometry of ProNGF in the medium conditioned with the MCF-7 cells (FIGS. 5A, 5C and 5E) or of recombinant ProNGF (FIGS. 5B and 5D), giving the relative abundance as a function of the mass, FIG. 6 represents a photograph of a Western blot showing the presence of Sortilin in the cancerous mammary epithelial cells (MCF-7, T47-D, BT-20 and MDA-MB-231) and the normal cells (NMEC cells), actin having been used as positive control, FIG. 7 represents a graph giving the number of MDA cells which are growing in EMEM culture medium after 24, 48 and 96 hours of culture, having been transfected either with culture medium alone (Mock), or with a negative control interfering RNA (siGFP, double-stranded RNA molecule composed of the partially complementary sequences SEQ ID No. 1 and SEQ ID No. 2 in which the nucleotide N represents thymine T), or with an interfering RNA which decreases the expression of Sortilin (siSORT, double-stranded RNA molecule composed of the partially complementary sequences SEQ ID No. 3 and SEQ ID No. 4 in which the base N represents thymine T),

```
Sequence siGFP:
                                         SEQ ID No. 1
5'-GCUGACCCUGAAGUUCAUCNN-3'

SEQ ID No. 2
5'-GAUGAACUUCAGGGUCAGCNN-3'

Sequence siSORT:
                                         SEQ ID No. 3
5'-GGUGGUGUUAACAGCAGAGNN-3'

SEQ ID No. 4
5'-CUCUGCUGUUAACACCACCNN-3'
```

Figure 8:
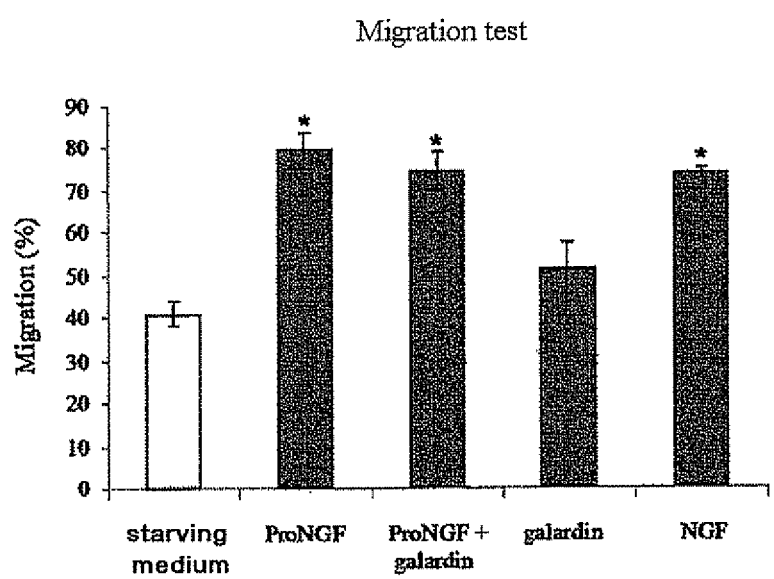
Figure 9:
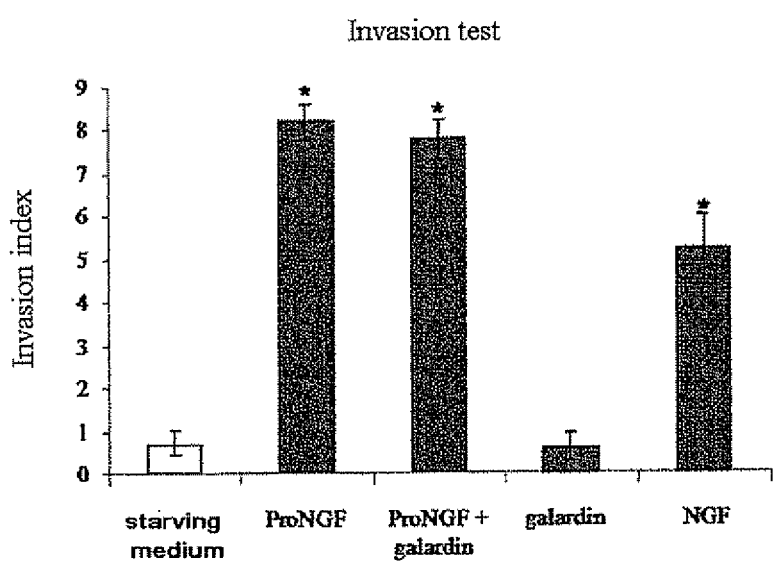
Figure 10:
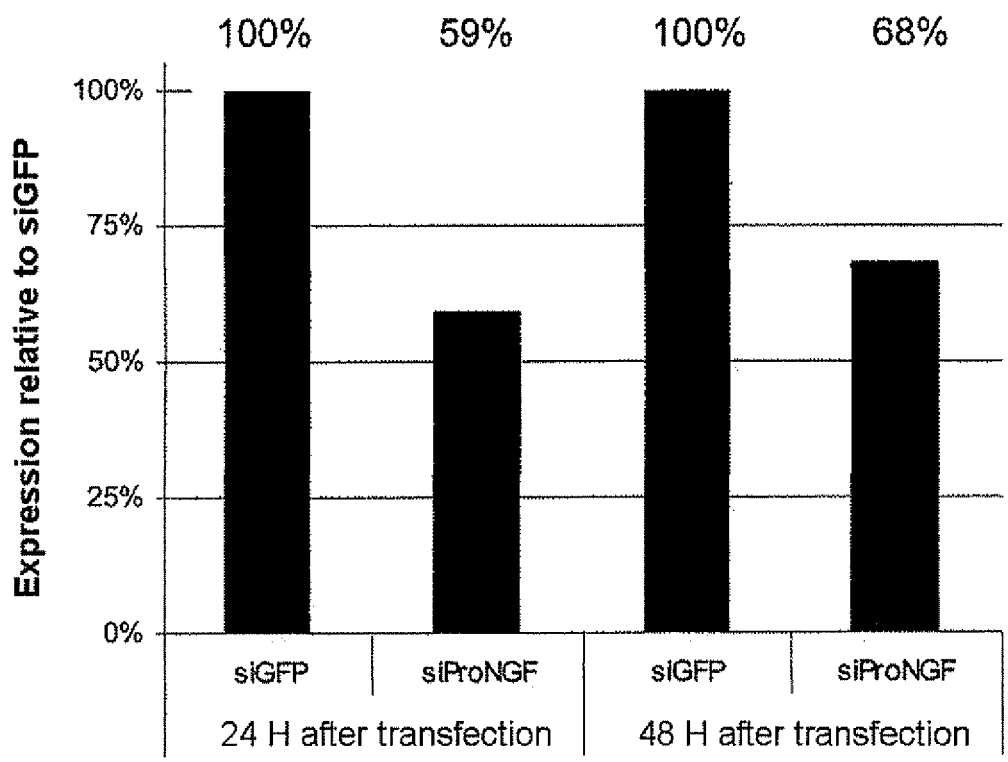

FIG. 8 represents a graph giving the percentage cell migration using MCF-7 cells bathed either in starving medium alone, or in starving medium supplemented with 200 ng/ml of ProNGF, or in starving medium supplemented with 200 ng/ml of ProNGF and 20 µM of galardin, or in starving medium supplemented with 20 µM of galardin, or in starving medium supplemented with 200 ng/ml of NGF, FIG. 9 represents a graph giving the invasion index using MCF-7 cells bathed either in starving medium alone, or in starving medium supplemented with 200 ng/ml of ProNGF, or in starving medium supplemented with 200 ng/ml of ProNGF and 20 µM of galardin, or in starving medium supplemented with 20 µM of galardin, or in starving medium supplemented with 200 ng/ml of NGF, and FIG. 10 plotted from the Western blot photographs shows the decrease in expression of ProNGF in the MCF-7 cells following transfection of a ProNGF interfering RNA (siProNGF), after 24 or 48 hours of culture. Actin was used as positive control for validating the equal loading. The MCF-7 cells were transfected with interfering RNAs (siRNAs) directed against GFP (siGFP, composed of the partially complementary sequences SEQ ID No. 1 and SEQ ID No. 2), or against ProNGF (siProNGF, double-stranded RNA molecule composed of the partially complementary sequences SEQ ID No. 5 and SEQ ID No. 6 in which the base N represents thymine T). The relative amount of ProNGF detected by blotting was evaluated with the QuantityOne software (Bio-Rad), related to the equal loading and presented in the form of a histogram where 100% is assigned to the siGFP control condition,

```
Sequence siGFP:
                                         SEQ ID No. 1
5'-GCUGACCCUGAAGUUCAUCNN-3'

SEQ ID No. 2
5'-GAUGAACUUCAGGGUCAGCNN-3'

Sequence siProNGF:
                                         SEQ ID No. 5
5'-CAGUGUAUUCAAACAGUAUNN-3'

SEQ ID No. 6
5'-GUACUGUUUGAAUACACUGNN-3'
```

EXAMPLE 1

Cell Culture

1.1. Material

The cells used are established breast cancer cell lines (BT-20, MCF-7, MDA-MB-231, T-47D) obtained from the ATCC (American Type Culture Collection) and NMEC (Normal Mammary Epithelial Cells) in primary culture, obtained from patients having undergone a mammoplasty at the Centre Oscar Lambret in Lille. The MCF-7, MDA-MB-231 and T-47D are epithelial cells which originate from pleural effusions in patients suffering from adenocarcinoma; the 13T-20, for their part, originate from a primary carcinoma. MCF-7 and T-47D are termed "hormone-sensitive" since they express oestrogen receptors, whereas BT-20 and MDA-MB-231 are termed "hormone-insensitive" since they do not express them.

The biopsies originate from patients having undergone a mammoplasty of nonmalignant tissue (Professeur Pellerin CHRU, Lille) or cancerous tissue exeresis (Docteur Laurent, Croisé Laroche, Marcq en Baroeul).

The immunohistochemistry slides (tissue array) containing spots of tumoral and normal breast tissues originate from Biochain Inc. (Cat. No. T8235731). Other immunohistochemistry slides containing tissues derived from various organs (cancerous tissues and corresponding normal tissues) originate from Superbio Chips (Cat. No. MA (cancer tissue), MAN (corresponding normal tissue) and AA (various normal organs)). Female six-week-old SCID (Severe Combined ImmunoDeficiency) mice were obtained from Iffa Credo (France) and acclimatized for at least two weeks. These mice were reared at 20-22° C., while maintaining alternating 12 h day/night (light from 6 am to 6 pm), and fed ad libitum, following the guidelines set by Institutional Animal Care.

The ProNGF used is human recombinant NGF sold by SCIL proteins (Germany). The recombinant EGF, HGF and NGF were obtained from R&D systems (France). The cortisol, the insulin, the DMSO (dimethyl sulfoxide), the cholera toxin, the transferrin, the C2 ceramide analog (N-acetyl-D-sphingosine), and the Hoechst 33258 (bisbenzimide) were obtained from Sigma (France). EMEM (Eagle's Minimum Essential Medium), DMEM/F12 (Dulbecco's Modified Eagle's Medium), trypsin-EDTA (ethylenediaminetetraacetate), HEPES (N2-hydroxyethylpiperazine-N'-2'-ethanesulfonic acid), L-glutamine, nonessential amino acids, penicillin/streptomycin and gentamycin are sold by Cambrex (France). The FCS (Foetal Calf Serum) is sold by Gibco Invitrogen Corporation (France). The various plastics used: 1 mL cryotubes, 15 mL and 50 mL centrifuge tubes, 100 mm diameter Petri dishes, 75 cm² dishes, 175 cm² dishes and 6-well plates (wells of 35 mm in diameter) are sold by Starstedt (Germany). The Transwell® are obtained from Costar (France). The fibronectin is obtained from Becton Dickinson (France). The glycergel is sold by Dako (France). The galardin is obtained from Tebu-Bio (France). The collagen type I is sold by Upstate (United States of America).

1.2. Thawing and Maintenance of Cells

The cell cryotubes are removed from the liquid nitrogen and thawed for 2 minutes at 37° C. The suspension is then recovered and transferred into a 50 mL centrifuge tube containing 19 mL of MEM (Minimum Essential Medium). The whole is centrifuged at 200 g (15 minutes) in order to remove the traces of DMSO (dimethyl sulfoxide). The cell pellet is recovered and then taken up with 10 mL of complete is medium (composition below) and transferred into a 75 cm² dish. The medium is changed after 24 hours, and 24 hours later, the cells are passaged. The cells are then maintained for two weeks before any experiments.

The cancer lines are maintained in 75 cm² dishes, on which they adhere and grow as a monolayer in a complete medium: EMEM supplemented with 10% FCS, 20 mM HEPES, 2 g/L of sodium bicarbonate, 2 mM L-glutamin, 1% nonessential amino acids, 40 µg/mL of penicillin/streptomycin and 50 µg/mL of gentamycin. The NMEC are maintained in 75 cm² dishes on which they adhere and grow as a monolayer in complete medium: DMEM/F12 supplemented with 5% FCS, 10 μg/mL of insulin, 5 μM cortisol, 2 ng/mL of EGF, 0.01 ng/mL of cholera toxin, 100 μg/mL of penicillin and 45 μg/mL of gentamycin.

The cells are cultured in a humid atmosphere at 37° C. and at 5% $CO_2$. The maintaining medium is changed every two days and the cells are passaged at confluence.

EXAMPLE 2

Detection of ProNGF 2.1. Methodology

Lysis of Mammary Cells and Biopsies: Protein Extraction

The cells are seeded in three Petri dishes 100 mm in diameter, and then, at 95% confluence, the cells are rinsed twice, on ice, with PBS (Phosphate Buffered Saline): 107 mM KCl, 59 mM $KH_2PO_4$, 137 mM NaCl, 56 mM $Na_2HPO_4$, and lysed with 100 μL/dish of a lysis buffer containing: 50 mM of tris-HCl, pH 7.5, 150 mM of NaCl, 1% Nonidet P40, 1% SDS (Sodium Dodecyl Sulfate), and proteasic activity inhibitors: 1 mM of phenylmethylsulfonide fluoride, 1 mM of orthovanadate, 1 mM of $Na_4P_2O_7$, 10 μg/mL of leupeptin and 10 μg/mL of aprotinin. The dishes are frozen for 12 hours and then scraped and the lysates are pooled, heated for 5 minutes at 100° C. and centrifuged at 10 000 g (10 min at 4° C.), and the supernatant is recovered.

The biopsies are weighed and placed, with ten times their volume of lysis buffer (described above), on a wheel (1 hour at 4° C.). They are then ground, on ice, with a dounce homogenizer, frozen (20 minutes at −80° C.), and thawed on ice. Finally, they are centrifuged at 13 000 g (10 minutes at 4° C.), a lipid disc is removed and the supernatant is recovered.

The supernatents are assayed by the bicinchoninic acid method compared with a range of bovine serum albumin, and then aliquoted in 50 μL aliquots before freezing.

Obtaining Conditioned Medium and Serum

The MCF-7 cells are seeded, in complete medium, into 175 $cm^2$ dishes. At 90% confluence, these dishes are rinsed twice in starving medium and then the cells undergo starving for 24 hours with 14 mL of starving medium. After this period, the medium conditioned by the cells is recovered and centrifuged at 1 000 g (15 minutes at 4° C.). The supernatant is then used directly, or frozen at −20° C. Concentrating/desalifying units with a cut-off threshold of 10 kDa (Centricon Plus 20, Millipore, France) are each loaded with 14 mL of MCF-7-conditioned medium and then centrifuged at 4 000 g (15 minutes at 4° C.). These same units were reloaded a further three times with 14 mL of conditioned medium (which results in a 4-fold concentration of the starting medium). The units are then desalified with mQ quality water (18.2 osm) by loading 14 mL and centrifuging at 4 000 g (15 minutes at 4° C.), this being done twice according to the manufacturer's recommendations. Finally, the concentrate is recovered by inversion of the unit and a centrifugation at 1 000 g (4 minutes at 4° C.); 250 μL are recovered. The concentrated conditioned medium is then aliquoted in 50 μL aliquots and frozen at −20° C. A concentration factor of 4×14 000/250, i.e. 224 times, is then achieved.

The MDA-MB-231 cells ($3\times10^6$) are resuspended in PBS and then injected subcutaneously in the flanks of eight-week-old SCID mice. The tumor volume is measured every two days, after two weeks. After seven weeks, the mice are anesthetized with ether, and the blood is collected by intracardiac sampling, before sacrifice of the animals. The blood is left overnight at 4° C. in order to allow clotting, the serum being recovered after centrifugation, assayed and frozen at −20° C.

SDS-PAGE

The aliquots (50 μL) are thawed before use, and taken up with 12.5 μL of 5×Laëmmli buffer: 5% SDS, 5% β-mercaptoethanol, 50% glycerol, 50 mM Tris, pH 6.8, 0.3% bromophenol blue. The proteins are loaded into the wells of a 12.5% polyacrilamide gel. After migration (at 30 mA, for 5 hours) and transfer onto a nitrocellulose membrane (at 200 mA, for 1 hour), the quality of the transfer is assessed by staining with Ponceau red.

Immunodetection

The membranes are saturated with 4% bovine serum albumin in TBS (Tris Buffered Saline) solution containing 0.1% Tween 20 (17.54 g NaCl, 2.42 g Tris, 2 mL tween 20, QSP 2 L, pH adjusted to 7.4) at ambient temperature for 2 hours. After saturation, the membranes are incubated overnight at 4° C. with the various primary antibodies: anti-ProNGF (AB9040 from Chemicon) at 1:2000, anti-NGF (SC-548 from Sigma) at 1:2000 or anti-actin (A-2066 from Sigma) at 1:5000 in the saturation solution. After rinsing with TBS 0.1% Tween 20, the membranes are incubated for 1 hour at ambient temperature with an anti-rabbit secondary antibody (A-1949 from Sigma, France) coupled to horseradish peroxidase, at 1:20 000 in the saturation solution. After rinsing, visualization is carried out with the ECL system (Pierce Interchim, France) according to the recommended data for use.

Immunohistochemistry

In a first step, the tissue array slides are deparaffinized. For this, they are incubated successively in the following baths for 10 minutes: methycyclohexane (twice), 100% ethanol, 95% ethanol, 70% ethanol, and water. The slides are then rinsed with TBS 0.1% Tween 20 (TBS-T) for 10 minutes, with agitation. The antigens are reactivated in 10 mM citrate buffer, pH6, by heating to 90° C. for 40 min, and then leaving to cool to ambient temperature for 30 min. The endogenous peroxidases are inhibited by incubation in TBS-T containing 3% of $H_2O_2$, for 5 min. The slides are then saturated with 3% BSA in TBS-T, for 1 h at 37° C., in a humid chamber. The slides are then incubated for 2 h with the anti-ProNGF primary antibody (AB9040 from Chemicon) diluted to 1/200 in TBS-T containing 3% BSA (incubation at 37° C. in a humid chamber). After three washes for 10 min with TBS-T, the slides are incubated for 2 h at 37° C. in a humid chamber with the anti-rabbit secondary antibody coupled to horseradish peroxidase (Cat. No. 711-035-152 Jackson Immunoresearch) diluted to 1/400 in the saturation solution. The slides are washed for three times 10 minutes in TBS-T, and then a further three times 10 min in PBS. Visualization is carried out with the Sigma Fast substrate (Cat. No. D-4168, Sigma-Aldrich) for 5 min. The staining is stopped by washing in PBS. Counterstaining is performed with Harris hematoxylin (Cat. No. MHS16, Sigma-Aldrich) for 30 sec. After washing with water and with PBS, the slides are mounted for observation under a microscope.

Mass Spectrometry (MS)

The MCF-7-conditioned medium is injected onto a C4 LC (Liquid Chromatography) nanocolumn (Dionex, France), which makes it possible to separate the whole proteins according to a gradient of increasing hydrophobicity. Thus, the most hydrophobic proteins are eluted last. Once separated, the whole proteins are ionized by nanoESI (Electro Spray Ionization), and they are then analyzed in an ion trap (LCQ Deca XP+™ station from Thermo Electron) according to their mass (m) and their charge (z). We used the SIM (Selected Ion Monitoring) scan technique, which makes it possible to scan only certain ions of interest. These multicharged ions, characteristic of recombinant ProNGF, were determined beforehand by nanoLC-nanoESI/MS. Once detected in the conditioned medium using SIM of the ProNGF, the corresponding multicharged mass spectrum is resolved so as to find the mass of the protein which generated this spectrum.

2.2. Results

Detection Using Epithelial Cells

50 μg of total protein extracts of mammary epithelial cells are loaded onto a gel for SDS-PAGE. After transfer onto a nitrocellulose membrane, immunodetection with the AB9040 antibody and the A-2066 antibody (equal loading control) is carried out. NMEC: normal mammary epithelial cells, BT-20, MCF-7, MDA-MB-231 and T-47D are cancerous mammary epithelial cell lines.

The results are given in FIG. 1, which represents a photograph of a Western blot showing the production of ProNGF by the cancerous mammary epithelial cells (MCF-7, T47-D, BT-20 and MDA-MB-231), but not by normal cells (NMEC cells), actin having been used as positive control.

Detection Using Mammary Biopsies, by Western Blotting

50 μg of protein extracts of biopsies are loaded onto a gel for SDS-PAGE. After transfer onto a nitrocellulose membrane, immunodetection with the AB9040 antibody and the A-2066 antibody (equal loading control) is carried out. SS-x: normal breast biopsy number x, ST-x: tumoral breast biopsy number x.

The results are given in FIG. 2, which represents a photograph of a Western blot showing the presence of ProNGF in the cancerous mammary biopsies (ST-1 to -4) but not in the normal biopsies (SS-1 to -4), actin having been used as positive control.

Detection Using Mammary Biopsies, by Immunohistochemistry

Tissue array slides were used to screen a large number of samples. These are mammary biopsies spotted onto slides. The tissue arrays used here contain 60 spots of biopsies corresponding to one control, four normal donors and 25 patients suffering from breast cancer, in duplicate. The characteristics of the patients and also the intensity of the immunolabeling with the anti-ProNGF antibody are given in table 1. In the mammary biopsies derived from normal donors, weak labeling is present (intensity + in 4/4 patients), whereas the signal is much stronger in the cancerous mammary tissues (intensity ++/+++ in 20/25 patients). Furthermore, the labeling profile is different between the two types of tissues: in the cancerous tissue, the labeling is essentially epithelial, whereas in the normal biopsies, it is not.

TABLE 1

Characteristics of mammary biopsies present on the breast cancer tissue array and intensity of immunohistochemical labeling with the anti-ProNGF antibody.

| Identifier | Diagnosis | Label of differentiation | TNM classification | Stage | Labeling intensity |
|---|---|---|---|---|---|
| HT00031 | Control | | | | 0 |
| HT00500 | Normal breast | | | | + |
| HT00501 | Normal breast | | | | + (no epithelium) |
| HT00502 | Normal breast | | | | + (no epithelium) |
| HT00503 | Normal breast | | | | + (no epithelium) |
| HT00509 | Invasive ductal carcinoma | Medium | T2N0M0 | IIB | 0 |
| HT00510 | Invasive ductal carcinoma | Medium | T2N0M0 | IIB | + + |
| HT00511 | Invasive lobular carcinoma | High | T2N11M0 | IIIB | + + |
| HT00512 | Invasive lobular carcinoma | High | T2N17M1 | IV | + + + |
| HT00513 | Invasive lobular carcinoma | Medium | T2N1M0 | IIB | + |
| HT00520 | Invasive ductal carcinoma | Medium | T2N1M0 | IIB | 0 |
| HT00521 | Invasive ductal carcinoma | Medium | T2N0M0 | IIB | + + |
| HT00522 | Invasive ductal carcinoma | Medium | T2N1M1 | IV | + + + |
| HT00523 | Invasive ductal carcinoma | Medium | T2N3M1 | IV | + + |
| HT00524 | Invasive ductal carcinoma | Medium | T2N4M1 | IV | + |
| HT00531 | Fibroadenoma | Unknown | T2N0M0 | IIB | 0 |
| HT00532 | Invasive ductal carcinoma | Medium | T2N2M0 | IIIA | + + |
| HT00533 | Invasive ductal carcinoma | Low | T2N0M0 | IIB | + + + |
| HT00534 | Invasive ductal carcinoma | Low | T2N1M0 | IIB | + + |
| HT00535 | Invasive ductal carcinoma | Medium-Low | T2N1M0 | IIB | + + + |
| HT00542 | Invasive ductal carcinoma | Medium | T2N0M0 | IIB | 0 |
| HT00543 | Invasive ductal carcinoma | Medium | T2N0M0 | IIB | + + + |
| HT00544 | Invasive ductal carcinoma | Medium | T2N0M0 | IIB | + + + |
| HT00545 | Invasive ductal carcinoma | Medium | T2N0M0 | IIB | + + + |
| HT00546 | Invasive ductal carcinoma | Medium | T2N0M0 | IIB | + + + |
| HT00553 | Invasive ductal carcinoma | Medium | T2N3M0 | IIIB | 0 |
| HT00554 | Invasive ductal carcinoma | Low | T2N1M0 | IIB | + + + |
| HT00555 | Invasive ductal carcinoma | Medium | T2N0M0 | IIB | + + + |
| HT00556 | Invasive ductal carcinoma | Medium | T2N0M0 | IIB | + + + |
| HT00557 | Invasive ductal carcinoma | Medium | T2N0M0 | IIB | + + + |

Detection Using Lung and Thyroid Biopsies, by Immunohistochemistry

Other tissue array slides were used to analyze the expression of ProNGF in cancer types other than breast cancer. We screened nine patients for each cancer and analyzed, in parallel, the tumoral tissue and the normal tissue taken from the same patient in proximity to the tumor. Thus, we were able to demonstrate an overexpression of ProNGF in the case of lung cancer and thyroid cancer. The characteristics of the patients and also the intensity of the immunolabeling with the anti-ProNGF antibody are given in table 2. For lung cancer as for thyroid cancer, the labeling is much stronger in the tumoral tissue than in the normal tissue in 7 patients out of 9. For the other patients (2/9 for each cancer), the signals keep the same intensity in the tumoral and normal tissues. It should be recalled that our analytical technique is only semiquantitative, and that it cannot reveal small differences in expression.

the membrane, after staining with Ponceau red, is shown. Cancerous: 6 sera from mice injected with MDA-MB-231 cells, Normal: 2 sera from mice injected with PBS.

TABLE 2

Characteristics of the lung and thyroid biopsies present on the tissue array and intensity of the immunohistochemical labeling with the anti-ProNGF antibody.

| Identifier | Diagnosis | Level of differentiation | TNM classification | Stage | Labeling intensity Cancerous tissue | Normal tissue |
|---|---|---|---|---|---|---|
| Lung cancers | | | | | | |
| P1 | Adenocarcinoma | High | T2N0M0 | IB | +++ | ++ |
| P2 | Large cell carcinoma | | T2N0M0 | IB | +++ | ++ |
| P3 | Epidermoid cancer | Medium | T2N0M0 | IB | +/++ | ++ |
| P4 | Epidermoid cancer | Medium | T2N1M0 | IIB | ++ | ++ |
| P5 | Epidermoid cancer | Medium | T4N0M0 | IIIB | ++ | + |
| P6 | Adenocarcinoma | High | T2N0M0 | IB | ++ | + |
| P7 | Epidermoid cancer | Medium | T2N1M0 | IIB | +++ | + |
| P8 | Epidermoid cancer | Medium | T3N2M0 | IIIA | +++ | + |
| P9 | Epidermoid cancer | High | T2N1M0 | IIB | +++ | + |
| Thyroid cancers | | | | | | |
| T1 | Papillary carcinoma | | T2N0M0 | I | ++ | + |
| T2 | Papillary carcinoma | | T2N0M0 | I | ++ | ++ |
| T3 | Papillary carcinoma | | T2N0M0 | I | +++ | +++ |
| T4 | Papillary carcinoma | | T2N0M0 | II | +++ | +/++ |
| T5 | Papillary carcinoma | | T2N0M0 | II | ++/+++ | + |
| T6 | Papillary carcinoma | | T3N1aM0 | III | +++ | + |
| T7 | Papillary carcinoma | | T1N0M0 | I | +++ | + |
| T8 | Papillary carcinoma | | T2N1bM0 | IVA | ++/+++ | + |
| T9 | Papillary carcinoma | | T3N0M0 | III | ++/+++ | + |

Secretion of ProNGF

In order to determine whether the ProNGF is secreted, we concentrated MCF-7-conditioned medium. To do this, 100 µL of conditioned medium concentrated 224 times are subjected, after electrophoresis and transfer, to immunodetection with the SC-548 antibody. Recombinant NGF and recombinant ProNGF were analyzed as controls.

The results are given in FIG. 3A, which represents a photograph of a Western blot showing the secretion of ProNGF by the MCF-7 cancerous cells and the absence of secretion of NGF (concentrated conditioned medium lane), the two lanes to the right being control lanes. It may be noted that no NGF secretion is observed here because the experiment is stopped too early to observe NGF due to the abundance of ProNGF. When the experiment is continued, a band for NGF is also observed. This demonstrates that, not only is ProNGF a tumor marker, but it is also secreted in large amounts.

To verify that the concentrating/desalifying unit used, with a cut-off threshold of 10 kDa, was capable of retaining NGF (13.6 kDa), we concentrated a mixture of recombinant ProNGF and recombinant NGF under the same experimental conditions: 20 ng of ProNGF and 20 ng of NGF were added to unconditioned medium and were then subjected to the same conditions as the conditioned medium.

The results (FIG. 3.B) prove that the concentrating/desalifying unit is capable of retaining NGF and ProNGF.

Detection in the Serum

100 µg of protein extracts of mouse sera are loaded onto a gel for SDS-PAGE. After transfer onto a nitrocellulose membrane, immunodetection with the AB9040 antibody is carried out. In the equal loading control, a band visible at 24 kDa on The results are given in FIG. 4, which shows that a band immunoreactive for ProNGF appears at 26 kDa (weight of ProNGF) in 5 out of 6 sera from mice injected with cancerous cells; and no band was detected in the sera from the control animals.

Detection by Mass Spectrometry

We carried out the procedure as indicated above. The results are given in FIG. 5, which represents graphs of detection, by mass spectrometry, of ProNGF in the MCF-7-conditioned medium (FIGS. 5A, 5C and 5E) or of recombinant ProNGF (FIGS. 5B and 5D), giving the relative abundance as a function of the mass. FIGS. 5A and B correspond to the protein fraction from the nanoLC corresponding to the SIM of at least one of the three characteristic ions of ProNGF. FIG. 5C corresponds to the mass spectrum of the protein eluted at 29.43 min in A. FIG. 5D corresponds to the mass spectrum of recombinant ProNGF with its three characteristics ions in red. Finally, FIG. 5E shows the deconvolution of the mass spectrum of the protein eluted at 29.43 min in A.

These results show that a protein corresponding to the SIM (Selected Ion Monitoring) of ProNGF, which is eluted at the same time (29.43 min, FIG. 5.A) as recombinant ProNGF (30.17 min, FIG. 5.B), appears in the MCF-7-conditioned medium. This protein, once ionized, generates the same multicharged ions (998.2, 1039.9, 1083.4, FIG. 5.C) as the recombinant ProNGF (996.2, 1037.5, 1082.6, FIG. 5D). Furthermore, the calculation by deconvolution of the mass of the protein gives a value of 25 971 Da (FIG. 5.E), Thus, these results show that, firstly, we indeed identified ProNGF in the MCF-7-conditioned medium, and that, secondly, the detection of ProNGF by mass spectrometry is possible.

EXAMPLE 3

ProNGF Therapeutic Target 3.1. Methodology

Expression of Sortilin, ProNGF Receptor

The methods for carrying out the protein extraction are identical to those described for ProNGF (see point 2.1 above).

For the Western blotting, the membranes are saturated with 4% bovine serum albumin in a solution of TBS (Tris Buffered Saline) 0.1% Tween 20 (17.54 g NaCl, 2.42 g Tris, 2 mL tween 20, QS 2 L, pH adjusted to 7.4) at ambient temperature for 2 hours. After saturation, the membranes are incubated overnight at 4° C. with the various primary antibodies: anti-Sortilin (BD612101 from BD Biosciences) at 1:2000, anti-Actin (A-2066 from Sigma) at 1:5000 in the saturation solution. After rinsing with TBS 0.1% Tween 20, the membranes are incubated for 1 hour at ambient temperature with an anti-rabbit secondary antibody (A-1949 from Sigma, France) coupled to horseradish peroxidase, at 1:20000 in the saturation solution. After rinsing, visualization is carried out with the ECL system (Pierce Interchim, France) according to the recommended data for use.

Transfection of Interfering RNA (siRNA)

The interfering RNA (siRNA) transfection experiments were carried out with the Cell Line Nucleofector kit from Amaxa and the corresponding electroporation apparatus. This system makes it possible to obtain a high efficiency of gene transfer to the nucleus (nucleofection).

The MDA-MB-231 cells are passaged 2 days before the transfection, so as to reach 80% confluence at the time of the experiment. The cells to be transfected are trypsinized and then counted. The cell pellet (1 million cells) is taken up in 100 µl of Nucleofector Kit V solution and 3 µg of siRNA are added. This cell suspension is transferred into an electroporation cuvette, placed in the Amaxa apparatus and electroporated according to the X-13 program. The cells are subsequently put back in culture in a well of a 6-well plate for 24-72 h. The cell proliferation is followed over time and the cells are counted at regular time intervals. Anti-Sortilin Western blotting is carried out on the lysates recovered at various times, according to the protocol described in the previous paragraph, "Expression of Sortilin".

The MCF-7 cells are passaged 3-4 days before transfection, so as to reach 50% confluence at the time of the experiment. Two million cells are taken up in 100 µl of Nucleofector Kit V solution and 3 µg of siRNA are added. The transfection program used on the Nucleofector is E-14. Anti-ProNGF Western blotting is carried out on the lysates recovered after 24 hours or after 48 hours, according to the protocol described in point 2.1. The relative amount of ProNGF detected by blotting is evaluated with the QuantityOne software (Bio-Rad), related to the equal loading (actin) and presented in the form of a histogram where 100% is assigned to the siGFP control condition.

ProNGF Biological Activity Measurements

A "starving" medium was used, "starving" denoting a medium identical to the complete medium but without serum and supplemented with 2 µg/mL of fibronectin and 30 µg/mL of transferrin. For the various biological activity measurements, the various test molecules (ProNGF, NGF and galardin) are added to this starving medium. During the treatments, the media are renewed every 24 hours.

Migration and Invasion

The migration and invasion tests are carried out as previously described by Bracke et al. (1999, J Natl Cancer Inst, 91: 354-359). The protocols for using Boyden chambers and for invasion in collagen gel are described below.

Boyden Chamber (Transwell®)

12-well plates containing Transwells® with a pore diameter of 12 µm are equilibrated with starving medium and placed at 37° C. under 5% $CO_2$ for 2 hours. The medium is then drawn off and replaced, in the lower chamber, by starving medium with the various test molecules, whereas, in the upper chamber, 40 000 cells are seeded in starving medium alone. After 24 hours, the Transwells® are rinsed with PBS, the upper face is scraped, and then Hoechst labeling is carried out (as described for the survival test), so as to visualize the cells that have crossed the membrane. The Transwells® are mounted between a slide and cover slip by means of a drop of glycergel heated to 55° C., and the slides are then conserved at 4° C. in the dark until counting. Each condition is carried out in duplicate; a minimum of 40 fields is counted for each condition. The data represent the mean, weighted by the standard deviations, of the counts on these 40 fields. They are provided as percentage migration where 100% migration is assigned to an HGF control at 50 ng/mL.

Collagen Gel Invasion Test

The collagen type I gel is prepared in the following way: 2.1 mL of collagen Type I, 0.8 mL of EMEM (10×), 4.6 mL of PBS, 0.8 mL of $NaHCO_3$ at 0.25 M and 0.15 mL of 1 M NaOH. 1.25 mL are deposited in the wells of a 6-well plate. Once the gel has solidified, 100 000 cells are seeded with starving medium and the various test molecules for 24 hours. The cells are subsequently counted and the invasion index is determined (number of deep cells related to the number of cells at the surface). Each condition is carried out in triplicate and a minimum of 45 fields is counted per condition.

3.2. Results

Expression of Sortilin, ProNGF Receptor

50 µg of total protein extracts of mammary epithelial cells are loaded onto a gel for SDS-PAGE. After transfer onto a nitrocellulose membrane, immunodetection with the BD612101 antibody and the A-2066 antibody (equal loading control) is carried out. NMEC: normal mammary epithelial cells, BT-20, MCF-7, MDA-MB-231 and T-47D are cancerous mammary epithelial cell lines.

The results are given in FIG. 6, which represents a photograph of a Western blot showing the presence of Sortilin in the cancerous mammary epithelial cells (MCF-7, T47-D, BT-20 and MDA-MB-231) and the normal cells (NMEC cells), actin having been used as positive control. Sortilin therefore appears in all these cells. On the other hand, this band appears to be more intense in the cancerous cells than in the normal cells, whereas the loading control, actin, does not vary. One may therefore think that there is less Sortilin in the normal mammary epithelial cells than in the cancerous cells.

Decrease in the Expression of Sortilin by Interfering RNA (Sortilin Knock Down)

MDA-MB-231 cells maintained in the EMEM culture medium were transfected either with culture medium alone (Mock), or with an interfering RNA directed against the GFP protein (siGFP) or with an interfering RNA directed against Sortilin (siSORT).

The results given in FIG. 7 show that, under the culture conditions chosen, the number of MDA-MB-231 cells in culture does not increase over time in the presence of siSORT. In the Mock or siGFP control groups, the number of cells doubles between 24 and 48 h of culture. The proliferation of the MDA-MB-231 cancerous mammary line is therefore slowed down by transfection of an interfering RNA directed against Sortilin. We verified by Western blotting that the siSORT transfection indeed decreased the level of expression of the Sortilin protein. Thus, this experiment allowed us to show that it was possible to control the abnormal proliferation of the breast cancer cells by targeting Sortilin, the ProNGF receptor, with an interfering RNA.

Migration

The effects of ProNGF on the migration of mammary epithelial cells were comprehended by means of tests in Boyden chambers (Transwell®). Each condition was carried out in duplicate and a minimum of 40 fields was counted. The MCF-7 cells were seeded in starving medium at the upper face of the Transwell®, whereas the lower face bathed in starving medium alone or with 200 ng/mL of ProNGF, or with 20 µM of galardin with or without 200 ng/mL of ProNGF, or with 200 ng/mL of NGF. The cells having crossed the Transwell® were then counted. *$p<0.05$, comparison with the starving medium alone condition.

The results are given in FIG. 8, which represents a graph giving the percentage cell migration using MCF-7 cells bathed in the various media. These results demonstrate that treatment of the MCF-7 cancerous cells with ProNGF makes it possible to increase their ability to migrate, in a similar manner to NGF at equal doses. The addition of galardin, which is capable of inhibiting the synthesis of NGF from ProNGF, to the culture medium tends to demonstrate that the promotion of the migratory activity is due to the ProNGF and not to the NGF that it is capable of generating.

Invasion

The invasive capacity of the ProNGF-stimulated MCF-7 cells was tested in collagen type I gel. Each condition is carried out in triplicate and a minimum of 45 fields is counted per condition. The MCF-7 cells are seeded onto a collagen type I gel in starving medium alone or with 200 ng/mL of ProNGF, or with 20 µM of galardin with or without 200 ng/mL of ProNGF, or with 200 ng/mL of NGF. *$p<0.05$, comparison with the starving medium alone condition.

The results are given in FIG. 9, which represents a graph showing the invasion index using MCF-7 cells bathed in the various media. These tests show that ProNGF stimulates MCF-7 invasion.

Decrease in the Expression of ProNGF by Interfering RNA

The MCF-7 cells were transfected with 3 µg interfering RNA (siRNA) directed against GFP (siGFP) or against ProNGF (siProNGF). After 24 to 48 h of culture, the cells were lysed and ProNGF Western blotting was carried out. The relative amount of ProNGF detected by blotting was evaluated with the QuantityOne software (Bio-Rad) related to the actin equal loading and presented in the form of a histogram where 100% is assigned to the siGFP control condition (FIG. 10). On the photographs of the blots, we were already able to observe that the transfection of siProNGF decreases the expression of the ProNGF protein in the MCF-7 cells. Densitometric analysis made it possible to evaluate this decrease at 59% after 24 h of transfection.

This experiment allowed us to show that it was possible to decrease the level of expression of ProNGF in breast cancer cells by using the interfering RNA strategy.

The invention claimed is:

1. A method for treating breast, thyroid, lung, or prostate cancer, comprising administering a pharmaceutical composition comprising a therapeutically effective amount of a nerve growth factor precursor (ProNGF) inhibitor to a patient having breast, thyroid, lung, or prostate cancer, wherein the ProNGF inhibitor is an siRNA that decreases expression of ProNGF or a ProNGF receptor.

2. The method as claimed in claim 1, wherein the amount is effective for blocking cancer cell migration or invasion in the patient.

3. The method as claimed in claim 1, wherein the ProNGF inhibitor specifically penetrates into cancer cells of the patient.

4. A method of inhibiting invasion or migration of cancer cells that produce and secrete nerve growth factor precursor (ProNGF), comprising providing a ProNGF inhibitor to the cancer cells to inhibit the invasion or migration of the cancer cells, wherein the ProNGF inhibitor is an siRNA that decreases expression of ProNGF or a ProNGF receptor.

5. The method as claimed in claim 1, wherein the method is for treating breast cancer.

6. The method as claimed in claim 1, wherein the siRNA decreases the expression of Sortilin.

7. The method as claimed in claim 1, wherein the siRNA decreases the expression of ProNGF.

8. The method as claimed in claim 4, wherein the cancer cells are breast, thyroid, lung, or prostate cancer cells.

9. The method as claimed in claim 4, wherein the cancer cells are breast cancer cells.

10. The method as claimed in claim 4, wherein the siRNA decreases the expression of Sortilin.

11. The method as claimed in claim 4, wherein the siRNA decreases the expression of ProNGF.

12. A method of inhibiting proliferation of cancer cells that produce and secrete nerve growth factor precursor (ProNGF) in a patient, comprising administering a pharmaceutical composition comprising an effective amount of a ProNGF inhibitor to the patient to inhibit proliferation of the cancer cells, wherein the ProNGF inhibitor is an siRNA that decreases expression of ProNGF or a ProNGF receptor.

13. The method as claimed in claim 12, wherein the patient has breast, thyroid, lung, or prostate cancer.

14. The method as claimed in claim 12, wherein the patient has breast cancer.

15. The method as claimed in claim 12, wherein the siRNA decreases the expression of Sortilin.

16. The method as claimed in claim 12, wherein the siRNA decreases the expression of ProNGF.

\* \* \* \* \*